(12) United States Patent
Arimitsu

(10) Patent No.: US 10,363,105 B2
(45) Date of Patent: Jul. 30, 2019

(54) VIBRATION ACTUATOR SUITABLE FOR USE IN MAGNETIC FIELD ENVIRONMENT AND MEDICAL SYSTEM

(71) Applicant: CANON KABUSHIKI KAISHA, Tokyo (JP)

(72) Inventor: Yasumichi Arimitsu, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 338 days.

(21) Appl. No.: 15/168,586

(22) Filed: May 31, 2016

(65) Prior Publication Data

US 2016/0354167 A1    Dec. 8, 2016

(30) Foreign Application Priority Data

Jun. 5, 2015    (JP) .................................. 2015-114697

(51) Int. Cl.
*H01L 41/04* (2006.01)
*H02N 2/16* (2006.01)
(Continued)

(52) U.S. Cl.
CPC .......... *A61B 34/30* (2016.02); *H01L 41/0475* (2013.01); *H02N 2/163* (2013.01); *A61B 2090/374* (2016.02)

(58) Field of Classification Search
CPC ........................ A61B 34/30; A61B 2090/374
(Continued)

(56) References Cited

U.S. PATENT DOCUMENTS 5,448,127 A * 9/1995 Kanazawa ............. H02N 2/163
                                                310/323.06
5,632,074 A   5/1997 Kanazawa
(Continued)

FOREIGN PATENT DOCUMENTS

CN        1750379 A    3/2006
CN      101443572 A    5/2009
(Continued)

OTHER PUBLICATIONS

Office Action dated Jun. 4, 2018, in Chinese Patent Application No. 201610373130.9.
(Continued)

*Primary Examiner* — J. San Martin
(74) *Attorney, Agent, or Firm* — Venable LLP

(57) ABSTRACT

In a vibration actuator suitable for use in a magnetic field environment, vibration is excited in a vibration element in pressure contact with a driven element, so as to cause relative movement of the driven element and the vibration element. The vibration element includes an elastic body, of which a main ingredient is electrically insulating, dielectric, or semi-conductive, and an electromechanical energy conversion element. A first electrode having an open loop structure is provided on a surface of a piezoelectric body of the electromechanical energy conversion element, through which surface the piezoelectric body is joined to the elastic body. Second electrodes are provided on the piezoelectric body in a manner opposed to the first electrode via the piezoelectric body. A conduction path electrically connects the first electrode and at least one of the second electrodes. A gap is formed between each of adjacent second electrodes.

22 Claims, 11 Drawing Sheets

(51) Int. Cl.
*A61B 34/30* (2016.01)
*H01L 41/047* (2006.01)
*A61B 90/00* (2016.01)

(58) Field of Classification Search
USPC .......................................................... 310/323
See application file for complete search history.

(56) References Cited

U.S. PATENT DOCUMENTS

| 8,142,370 | B2 | 3/2012 | Weinberg et al. | |
| 9,417,424 | B2 | 8/2016 | Sumitomo | |
| 9,837,936 | B2 | 12/2017 | Arimitsu | |
| 2014/0125199 | A1* | 5/2014 | Furuta | C04B 35/4682 310/323.06 |
| 2015/0018840 | A1* | 1/2015 | Monfaredi | A61B 34/30 606/130 |
| 2015/0349666 | A1* | 12/2015 | Ifuku | H01L 41/257 310/323.06 |

FOREIGN PATENT DOCUMENTS

| CN | 102843062 A | 12/2012 |
| JP | 4-21371 A | 1/1992 |
| JP | 9-285151 A | 10/1997 |
| JP | 11-252956 A | 9/1999 |
| JP | 2007-159211 A | 6/2007 |
| JP | 2008-130767 A | 6/2008 |
| JP | 2014-000115 A | 1/2014 |

OTHER PUBLICATIONS

Office Action dated Feb. 26, 2019, in Japanese Patent Application No. 2015-114697.

U.S. Appl. No. 15/168,602, Yasumichi Arimitsu, filed May 31, 2016.

* cited by examiner

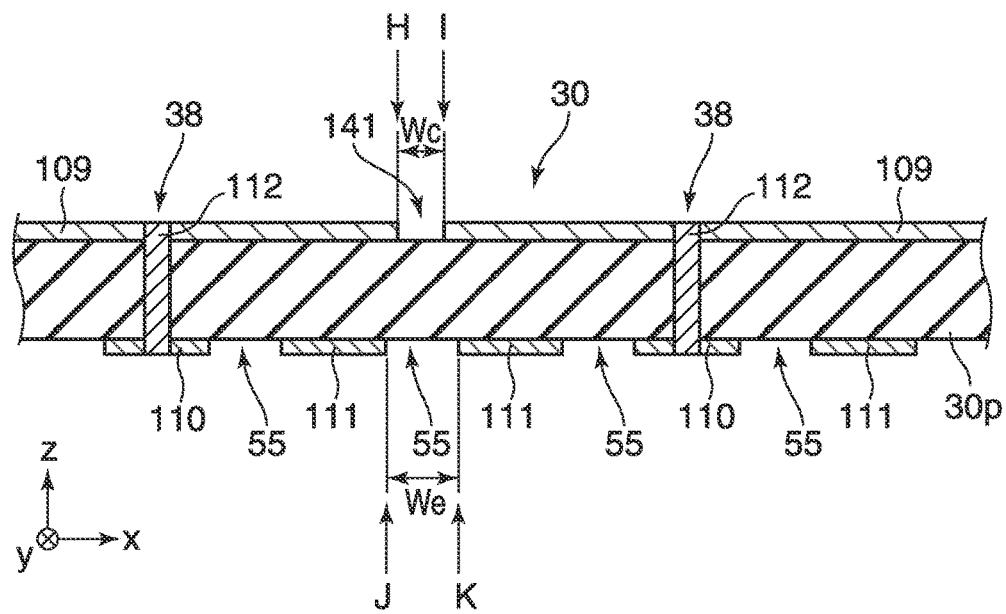
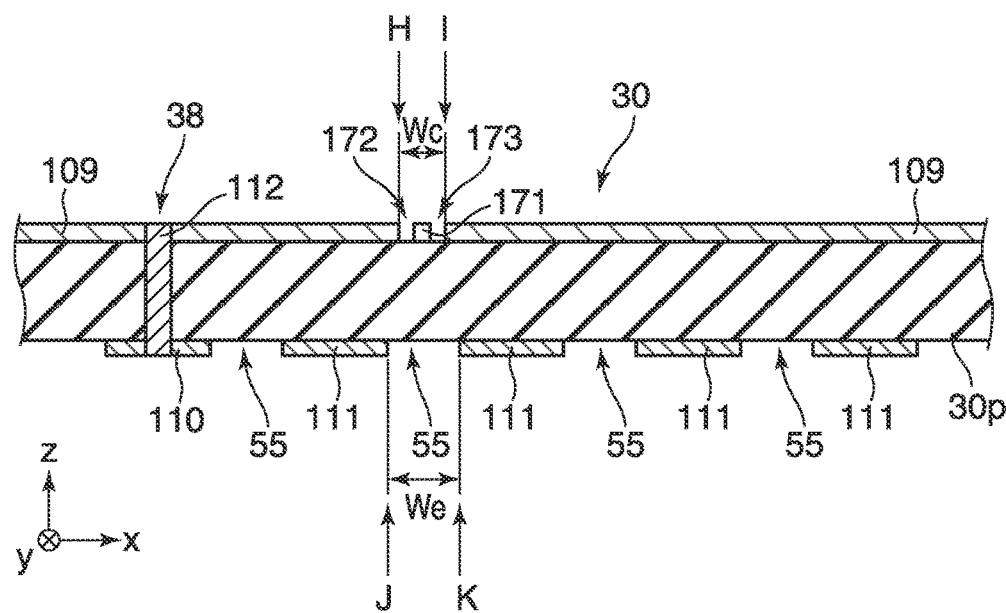

VIBRATION ACTUATOR SUITABLE FOR USE IN MAGNETIC FIELD ENVIRONMENT AND MEDICAL SYSTEM

BACKGROUND OF THE INVENTION

Field of the Invention

The present invention relates to a vibration actuator suitable for use in a magnetic field environment, which brings a vibration element and a driven element into pressure contact with each other and excites vibration in the vibration element to thereby move the vibration element and the driven element relative to each other, and a medical system provided with the vibration actuator.

Description of the Related Art

In recent years, research and development of a medical assistant robot for performing medical practice on a subject (patient) while acquiring a diagnostic image of the subject by using a magnetic resonance imaging diagnostic apparatus (hereinafter referred to as the "MRI diagnostic apparatus") have been actively performed. Further, an open-type MRI diagnostic apparatus provided with a gantry having a large opening or a gantry having a large space in the center thereof has come into wide-spread use, and there is an increasing possibility of intervention of a medical assistant robot or a doctor into the MRI diagnosis.

The static magnetic field generated by the MRI diagnostic apparatus has so large a magnitude as approximately 1.5 [T] to 3.0 [T] and is very strong. Further, in the MRI diagnostic apparatus, to determine three-dimensional position information which is used in acquiring a diagnostic image of a subject, with high accuracy, the magnetic field accuracy is controlled with very high accuracy, and a gradient magnetic field that varies with time in three axial directions is generated. Therefore, when a conductive material is used for a member that forms a closed loop in any of a medical assistant robot and other medical instruments, which is brought into the vicinity or the inside of the gantry of the MRI diagnostic apparatus, it is required to prevent the Lorentz force from being generated by a variable magnetic field and the conductive material from adversely affecting the variable magnetic field.

As an actuator used in a variable magnetic field environment which is controlled with high accuracy, there has been proposed a vibration actuator using an electromechanical energy conversion element which is typically formed e.g. of piezoelectric ceramics. Differently from an electromagnetic motor, the vibration actuator frictionally drives a driven element using vibration excited in a vibration element. Therefore, the vibration actuator has features that it generates a high thrust or torque in a low-speed region, with high responsiveness, and is capable of directly driving the driven element without using mechanical transmission means, such as a gear or a belt. The vibration actuator also has an advantage that a holding force or a holding torque is generated by friction between the vibration element and the driven element in a power-off state, and hence there is no need to use braking means, such as a brake.

In a type of the vibration actuator, a vibration element is formed by joining a piezoelectric element to an elastic body made of metal or the like, and AC voltages, which are different in phase, are applied to the piezoelectric element to thereby excite vibration in the vibration element in a specific vibration mode. In such a vibration actuator, an elliptic motion is generated on a surface of the elastic body which is in contact with the driven element, whereby the vibration element and the driven element are rotationally or linearly moved relative to each other.

As an example of the vibration actuator, there has been disclosed in Japanese Patent Laid-Open Publication No. 2007-159211 a vibration actuator that uses a vibration element having an annular shape, and an elastic body made of a metallic material having a high resonance sharpness (e.g. a steel material, such as stainless steel) is used in the annular vibration element. To cause the piezoelectric element to generate flexural vibration, such as bending vibration, it is necessary to generate a potential difference in a piezoelectric body (piezoelectric ceramics) as a component of the piezoelectric element. For this reason, in Japanese Patent Laid-Open Publication No. 2007-159211, a GND (ground) portion of the piezoelectric element and the elastic body are electrically connected to each other by a conductive junction made of a conductive material, such as solder, to ground the elastic body, whereby connection of the piezoelectric element to the GND potential is realized by making use of conductivity of the elastic body.

However, in the case where the vibration actuator including such a vibration element formed by using a metallic material having a high resonance sharpness as described in Japanese Patent Laid-Open Publication No. 2007-159211 is installed within or in the vicinity of the gantry of the MRI diagnostic apparatus, there are brought about, for example, three problems described below.

Firstly, disturbance may be caused in a magnetic field of the MRI diagnostic apparatus, which is controlled with high accuracy. More specifically, in a case where a member made of a conductive material includes a portion which has an annular shape, forming a closed loop, variable current flowing through the closed loop generates a new variable magnetic field by an induced electromotive force generated due to temporal variation in magnetic flux penetrating this closed loop. Therefore, the member having a closed loop portion, made of a conductive material, may disturb a magnetic field of the MRI diagnostic apparatus, which is necessary for encoding of spatial coordinates and is controlled with high accuracy.

Secondly, noise may be superimposed on a diagnostic image. More specifically, in a case where a member made of a conductive material includes a closed loop portion, an induced electromotive force is generated due to temporal variation in all magnetic fluxes penetrating the closed loop according to the Maxwell-Ampere law. Thus generated induced electromotive force generates electromagnetic waves due to variable current flowing through the closed loop, and these electromagnetic waves may be superimposed on various signals as electromagnetic noise. Therefore, the member having a closed loop portion made of a conductive material can be a source of noise for the MRI diagnostic apparatus and the peripheral devices.

Thirdly, unnecessary mechanical vibrations may be generated. More specifically, in a case where a member made of a conductive material has a closed loop portion, if a magnetic flux penetrating the closed loop temporally varies, the above-mentioned induced electromotive force causes a temporally varying current to flow through the closed loop portion. As a result, assuming that a current vector is represented by I and a magnetic flux vector by B, the Lorentz force F which temporally varies is applied to the closed loop in a direction of a vector product of I×B, which may cause unnecessary mechanical vibrations. Therefore, there is a possibility that the member having a closed loop portion made of a conductive material adversely affects the performances of the vibration actuator and the medical assistant robot.

To avoid these problems, it is envisaged to use a non-magnetic dielectric (insulating) material, such as engineering ceramics, engineering plastics, or a composite material (e.g. FRP (fibre-reinforced plastic)), for the component members of the vibration actuator, including the driven element and the elastic body. However, for example, in a case where the elastic body is dielectric, the GND portion of the piezoelectric element cannot be grounded via the elastic body as described in Japanese Patent Laid-Open Publication No. 2007-159211.

SUMMARY OF THE INVENTION

The present invention provides a vibration actuator suitable for use in a magnetic field environment, and a medical system provided with the vibration actuator.

In a first aspect of the invention, there is provided a vibration actuator in which a vibration element and a driven element are brought into pressure contact with each other, and vibration is excited in the vibration element to thereby move the driven element and the vibration element relative to each other, the vibration element comprising an elastic body of which a main ingredient comprises a material which is electrically insulating, dielectric, or semi-conductive, and an electromechanical energy conversion element that is joined to the elastic body, the electromechanical energy conversion element comprising a piezoelectric body, a first electrode that is provided on a surface of the piezoelectric body, via which surface the piezoelectric body is joined to the elastic body, the first electrode having an open loop structure, at least two second electrodes that are provided in a manner opposed to the first electrode via the piezoelectric body, and a conduction path that electrically connects the first electrode and at least one second electrode of the at least two second electrodes, wherein a gap is formed between the at least two second electrodes.

In a second aspect of the invention, there is provided a medical system including an articulated robot that performs diagnosis or an operation on a subject, the articulated robot having a plurality of joints, and a vibration actuator in which a vibration element and a driven element are brought into pressure contact with each other, and vibration is excited in the vibration element to thereby move the driven element and the vibration element relative to each other, the vibration actuator being assembled into each joint for enabling the joint to perform rotational movement, the vibration element comprising an elastic body of which a main ingredient comprises a material which is electrically insulating, dielectric, or semi-conductive, and an electromechanical energy conversion element that is joined to the elastic body, the electromechanical energy conversion element comprising a piezoelectric body, a first electrode that is provided on a surface of the piezoelectric body, via which surface the piezoelectric body is joined to the elastic body, the first electrode having an open loop structure, at least two second electrodes that are provided in a manner opposed to the first electrode via the piezoelectric body, and a conduction path that electrically connects the first electrode and at least one second electrode of the at least two second electrodes, wherein a gap is formed between the at least two second electrodes.

According to the present invention, the electrodes of the electromechanical energy conversion element as components of the vibration actuator are formed to have an open loop structure, and further, the elastic body joined to the electromechanical energy conversion element is formed of a material which is electrically insulating, dielectric, or semi-conductive. This makes it possible to realize a vibration actuator suitable for a variable magnetic field environment. For example, even when a manipulator provided with the vibration actuator is installed in the vicinity of or inside a gantry of an MRI diagnostic apparatus, it is possible to reduce the adverse influence of noise and vibration on the MRI diagnostic apparatus and the peripheral devices.

Further features of the present invention will become apparent from the following description of exemplary embodiments (with reference to the attached drawings).

BRIEF DESCRIPTION OF THE DRAWINGS

FIG. 6 is a partial cross-sectional view of a second electrode structure of the piezoelectric element.

FIG. 7 is a partial cross-sectional view of a third electrode structure of the piezoelectric element.

DESCRIPTION OF THE EMBODIMENTS

The present invention will now be described in detail below with reference to the accompanying drawings showing embodiments thereof.

Figure 1A:
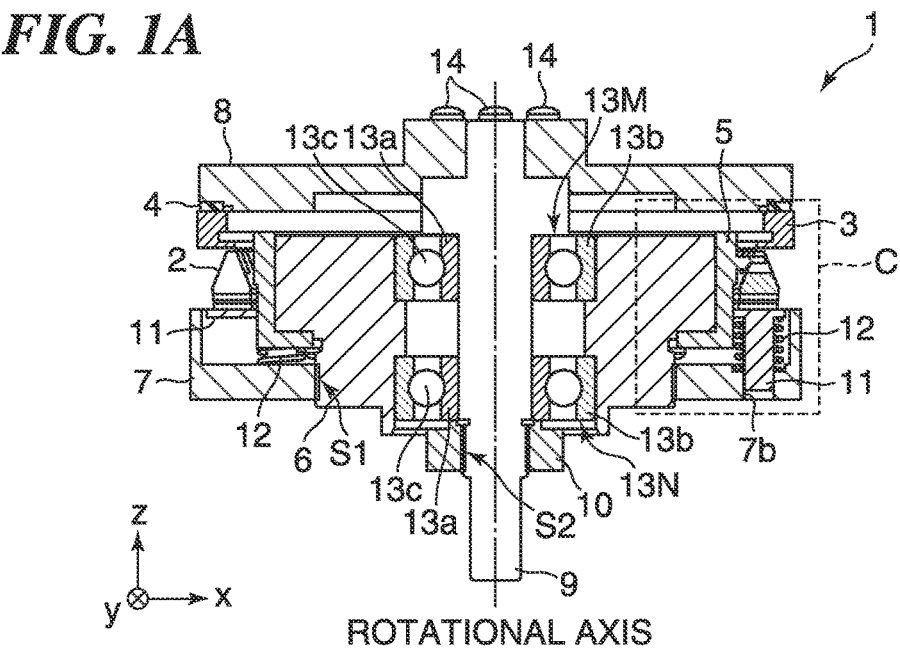
FIG. 1A is a schematic cross-sectional view of a vibration actuator according to an embodiment of the present invention.
Figure 1B:
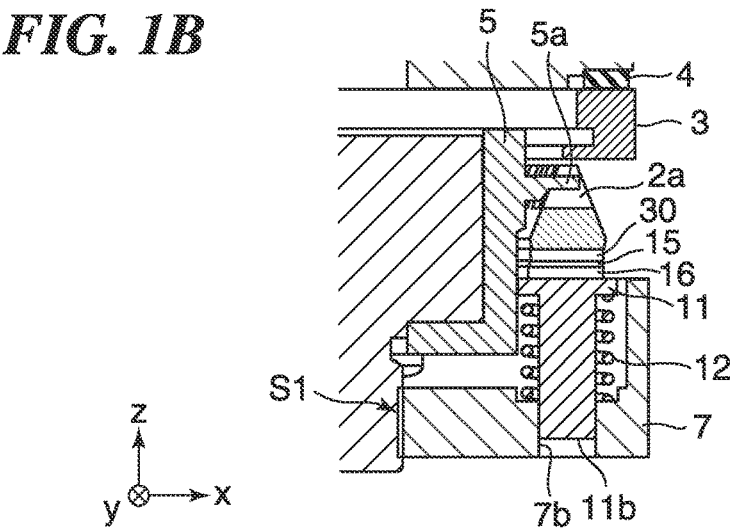
FIG. 1B is a partial enlarged view of an area C of the vibration actuator, which is surrounded by a broken line in FIG. 1A.
Figure 1C:
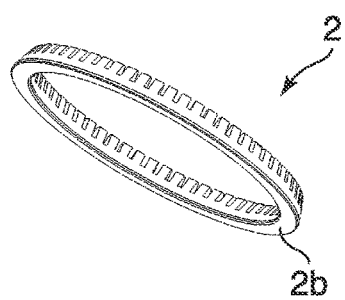
FIG. 1C is a perspective view of an elastic body as a component of the vibration actuator.

FIG. 1A is a schematic cross-sectional view of a vibration actuator 1 according to an embodiment of the present invention. FIG. 1B is an enlarged cross-sectional view of an area C surrounded by a broken line in FIG. 1A. FIG. 1C is a perspective view of an elastic body 2 as a component of the vibration actuator 1. As to the configuration of the vibration actuator 1, an x direction, a y direction, and a z direction, which are orthogonal to each other, are defined as shown in FIG. 1A, for convenience' sake.

The vibration actuator 1 includes the elastic body 2, a driven element 3, an anti-vibration rubber 4, a rotation stopping member 5, a housing 6, a supporting member 7, a flange 8, an output shaft 9, a preload member 10, a pressing member 11, coil springs 12, rolling bearings 13M and 13N, fastening members 14, a nonwoven fabric 16, and a piezoelectric element 30.

The two rolling bearings 13M and 13N each include an inner ring 13a, an outer ring 13b, and balls 13c which are held between the inner ring 13a and the outer ring 13b in pressure contact with each other. The outer ring 13b is fitted in the inner periphery of the housing 6, which has a hollow cylindrical shape, and the inner ring 13a is fitted on the output shaft 9. The output shaft 9 has an external thread formed thereon at a location close to the rolling bearing 13N, and the external thread is screwed into an internal thread formed in an inner hole of the preload member 10 to thereby form a threaded engagement portion S2. The preload member 10 applies a preload such that the inner rings 13a of the rolling bearings 13M and 13N are brought toward each other in the z direction. Thus, the rolling of the balls 13c of the two rolling bearings 13M and 13N enables the housing 6 and the output shaft 9 to be smoothly moved relative to each other about a rotational axis indicated by a one-dot-chain line without looseness. In the present embodiment, it is assumed that the supporting member 7 (or the housing 6) is secured to a supporting member, not shown, and the output shaft 9 is rotationally moved relative to the housing 6.

The flange 8 is fixed to one end of the output shaft 9 with the fastening members 14, such as screws or bolts. The anti-vibration rubber 4, which has an annular shape, is affixed to the flange 8, and is bought into friction contact with the driven element 3, which has an annular disk shape, fitted on the output shaft 9. The anti-vibration rubber 4 has a large friction coefficient, which enables the driven element 3 and the flange 8 to rotate in unison via the anti-vibration rubber 4 without slipping, and further, the anti-vibration rubber 4 can suppress unnecessary transmission of vibration from the driven element 3 to the flange 8.

A vibration element formed by the elastic body 2, which has an annular shape, and the piezoelectric element 30, which has an annular shape, is arranged in a manner surrounding the housing 6. The rotation stopping member 5 is fixed on an outer periphery of the housing 6, and lugs 5a protruding in a radial direction from an outer peripheral surface of the rotation stopping member 5 are inserted in grooves 2a formed in the elastic body 2, whereby the elastic body 2 is restricted from rotating in a circumferential direction.

The piezoelectric element 30, which is an electromechanical energy conversion element, is joined to a rear surface 2b of the elastic body 2 with an adhesive, and the vibration element is formed by the elastic body 2 and the piezoelectric element 30. A flexible circuit board 15 having wiring for supplying a voltage to the piezoelectric element 30 is affixed to the piezoelectric element 30 with an adhesive.

The pressing member 11, which has an annular shape, for pressing the vibration element against the driven element 3 in the z direction to thereby bring the elastic body 2 and the driven element 3 into pressure contact with each other is supported by the supporting member 7, which has an annular shape, arranged on an outer peripheral surface of the housing 6. The supporting member 7 has an internal thread formed on an inner peripheral surface thereof, and the internal thread is screwed into an external thread formed on an outer peripheral surface of the housing 6 to thereby form a threaded engagement portion S1, whereby the supporting member 7 is positioned in the z direction and is secured to the housing 6.

The pressing member 11 is provided with a plurality of protruding portions 11b, each of which have a bar shape, extending in the z direction at circumferentially equally-spaced intervals. Further, the supporting member 7 is formed with holes 7b in which the protruding portions 11b are inserted, respectively. The protruding portions 11b and the holes 7b function as a guide for guiding the pressing member 11 in the z direction. The coil springs 12 are inserted on the plurality of protruding portions 11b, respectively, and the compression length of each coil spring 12 can be adjusted by adjusting the position of the supporting member 7 in the z direction, whereby it is possible to adjust an urging force of the elastic body 2 applied to the driven element 3. The nonwoven fabric 16 as a cushioning member is disposed between the pressing member 11 and the flexible circuit board 15.

Although in the present example, the coil spring 12 is used as means for pressing the elastic body 2 against the driven element 3, this is not limitative, but any of various components having spring property, such as a disc spring, a wave washer, a spring washer, and a leaf spring, can be used.

Next, materials used for the components of the vibration actuator 1 will be described. As a material forming the main ingredient of the elastic body 2, there may be mentioned not a conductor, such as metal, but a material which is electrically insulating, dielectric, or semi-conductive, such as high-toughness ceramics, engineering plastics, and a semiconductor. In the description of the present embodiment, the main ingredient of a member A refers to a material forming half or more of substances constituting the member A, and is not required to be a single substance. Therefore, the definition that the main ingredient of the elastic body 2 is a material which is electrically insulating, dielectric, or semi-conductive is intended to mean that half or more of the substances constituting the elastic body 2 are only required to be one or a plurality of electrically insulating, dielectric, or semi-conductive materials. Further, what is meant by a description that the elastic body 2 is formed of an electrically insulating, dielectric, or semi-conductive material includes a case where the elastic body 2 contains other substances as impurities.

As an example of the high-toughness ceramics, there may be mentioned partially stabilized zirconia (PSZ). As an example of the engineering plastics, there may be mentioned fiber reinforced plastics (FRP), such as polyether-ether-ketone containing approximately 30 weight % of carbon fiber (PEEK-CF 30). An example of the semiconductor, there may be mentioned silicon carbide (SiC).

Further, in a case where the elastic body 2 is formed of an electrically insulating, dielectric, or semi-conductive material, it is more difficult to perform grounding (electrical conduction to an electrode of the flexible circuit board 15) using the elastic body 2, and hence the advantageous effect of the present invention is more remarkably exhibited. Here, what is meant by a description that the elastic body 2 is formed of an electrically insulating, dielectric, or semi-conductive material includes a case where the elastic body 2 contains other substances as impurities.

It is desirable that the driven element 3 has stable sliding characteristics and wear resistance characteristics in friction sliding with the elastic body 2. For the driven element 3, there are used engineering ceramics, such as alumina (aluminum oxide) and silicon nitride ($Si_3N_4$), engineering plastics, such as the above-mentioned PEEK-CF 30, or partially stabilized zirconia. To ensure good friction condition between the elastic body 2 and the driven element 3, a friction member, not shown, may be additionally provided on at least one of sliding surfaces of the elastic body 2 and the driven element 3.

For the anti-vibration rubber 4, butyl rubber, for example, is used. As the nonwoven fabric 16, there can be used a nonwoven fabric formed of felt, such as wool felt, or glass wool. The flexible circuit board 15 is made by forming an electric circuit on a polyimide (PI) film base, using copper foil, and it is desirable that exposed portions of the electric circuit are subjected to plating treatment (e.g. gold plating) in order to suppress oxidization. As the coil springs 12, coil springs formed of general spring steel material can be used, and coil springs formed of partially stabilized zirconia or engineering ceramics, such as silicon nitride, can also be used. Although a material selected from metal, resin, ceramics, etc., is used for each of other components, as required, when metal is used, it is desirable to design the component such that a closed conductive loop is not formed.

Next, configuration examples of the piezoelectric element 30 will be described. The piezoelectric element 30 has a structure in which electrodes are formed on a pair of opposite surfaces (e.g. front and rear surfaces) of a piezoelectric body, and in this description, it is assumed that the piezoelectric body is made of piezoelectric ceramics. However, the piezoelectric body is not limited to that made of piezoelectric ceramics.

Figure 2A:
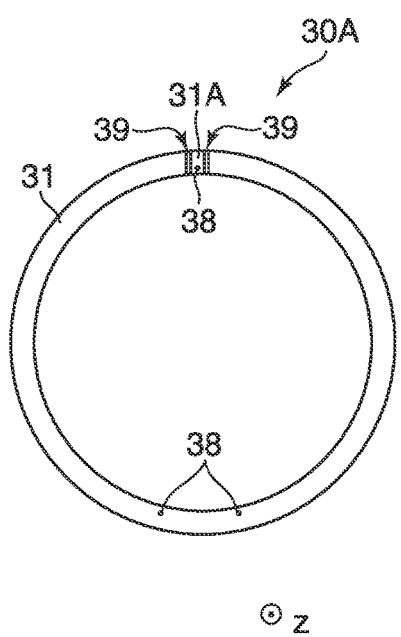
FIG. 2A is a plan view of a rear-side structure of a first example of the configuration of the vibration actuator shown in FIG. 1A.
Figure 2B:
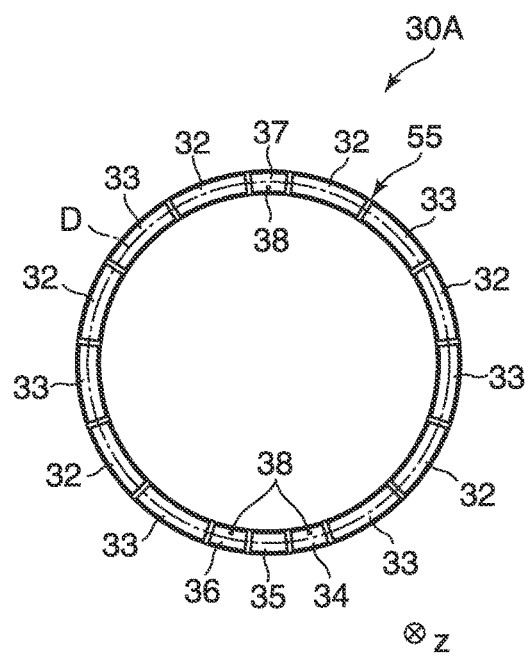
FIG. 2B is a plan view of a front-side structure of the first example of the configuration of the piezoelectric element.
Figure 2C:
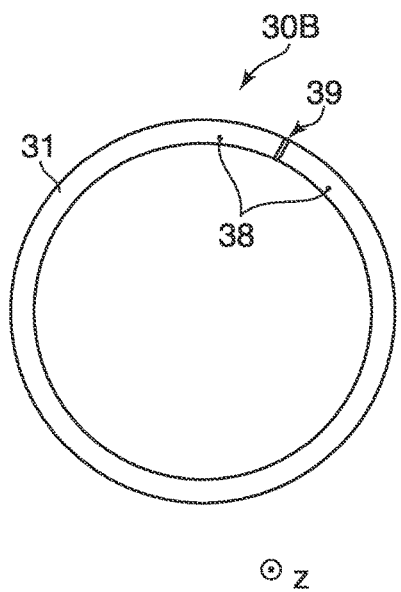
FIG. 2C is a plan view of a rear-side structure of a second example of the configuration of the piezoelectric element.
Figure 2D:
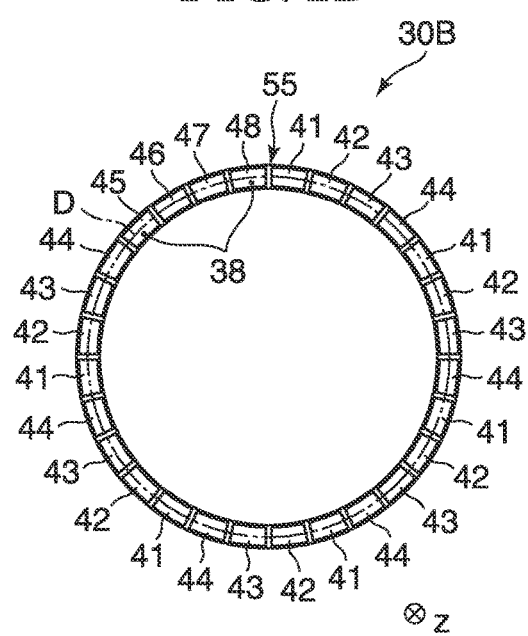
FIG. 2D is a plan view of a front-side structure of the second example of the configuration of the piezoelectric element.
Figure 3A:
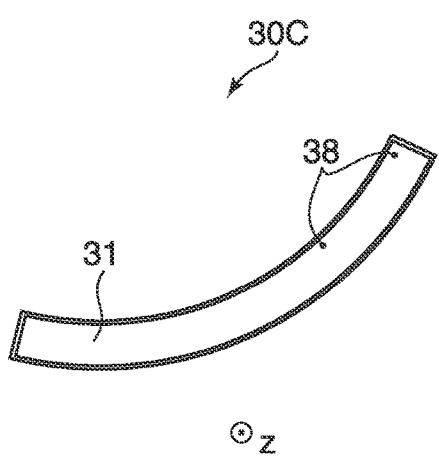
FIG. 3A is a plan view of a rear-side structure of a third example of the configuration of the piezoelectric element.
Figure 3B:
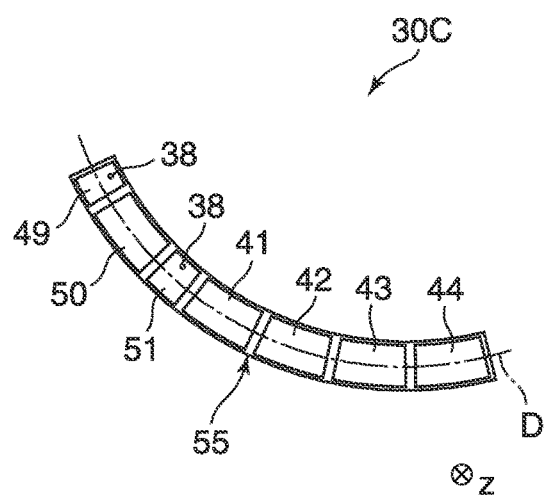
FIG. 3B is a plan view of a front-side structure of the third example of the configuration of the piezoelectric element.
Figure 4A:
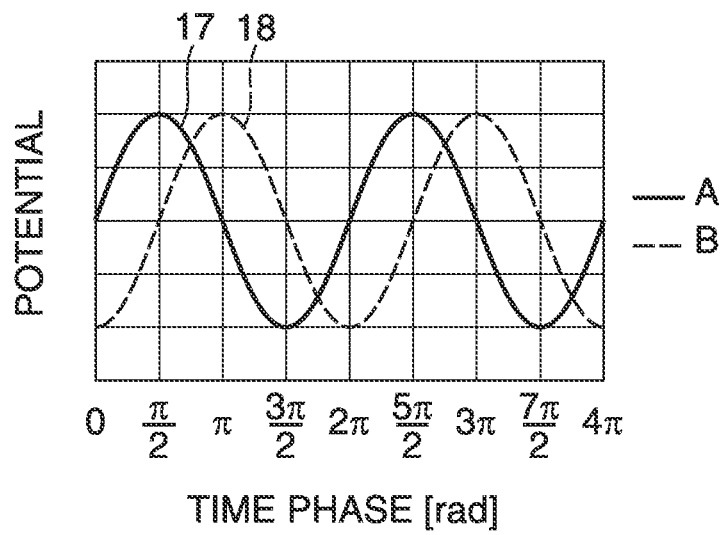
FIG. 4A is a diagram showing an example of AC voltages applied to the piezoelectric element included in the vibration actuator.
Figure 4B:
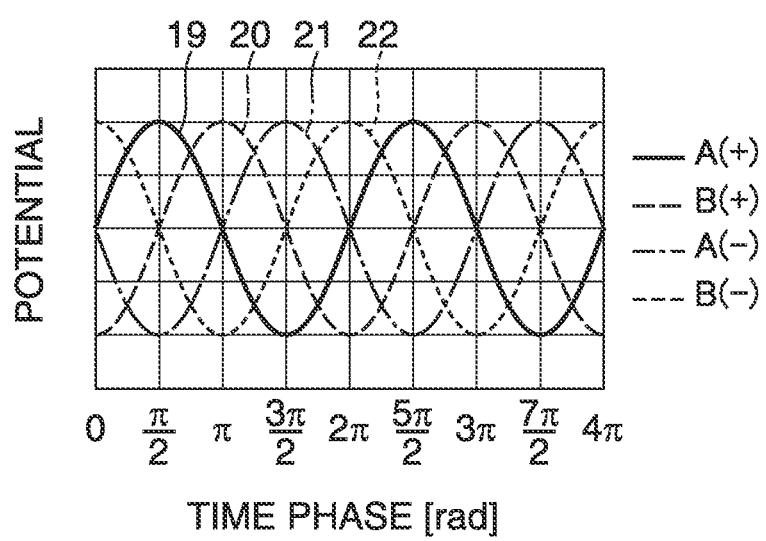
FIG. 4B is a diagram showing another example of the AC voltages applied to the piezoelectric element.
Figure 4C:
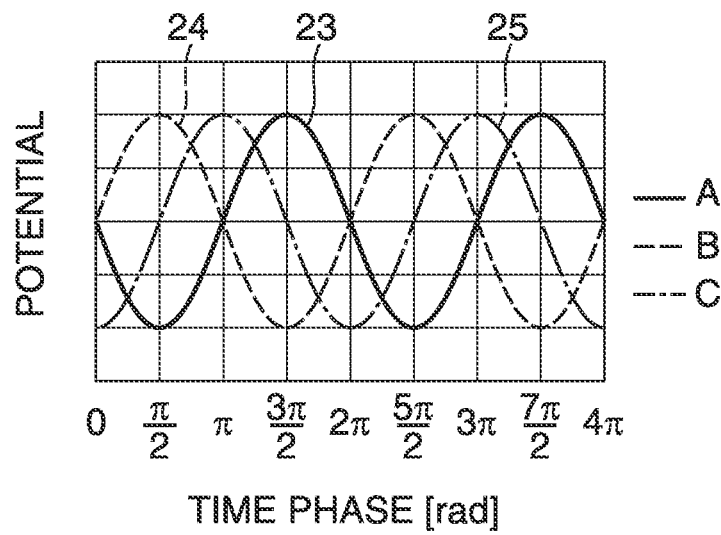
FIG. 4C is a diagram showing still another example of the AC voltages applied to the piezoelectric element.

FIGS. 2A and 2B are plan views each showing a first example of the configuration of the piezoelectric element 30, and FIGS. 2C and 2D are plan views each showing a second example of the configuration of the piezoelectric element 30. FIGS. 3A and 3B are plan views each showing a third example of the configuration of the piezoelectric element 30. In the third example of the configuration of the piezoelectric element 30, vibration of an out-of-plane deformation mode is excited for forming sine wave-like waves corresponding to seven wavelengths ($7\lambda$) in the circumferential direction of the elastic body 2. FIGS. 4A to 4C are diagrams each showing an example of AC voltages applied to the piezoelectric element shown in FIGS. 2A to 3B, and FIG. 4D is a diagram showing an example of a potential difference generated between the electrodes of the piezoelectric element.

First, a description will be given of the piezoelectric element, denoted by reference numeral 30A, according to the first example of the configuration (hereafter referred to as "the first configuration example") shown in FIGS. 2A and 2B. The piezoelectric element 30A has a structure in which the electrodes are formed on front and rear surfaces of piezoelectric ceramics having an annular plate shape, respectively. As the piezoelectric ceramics, lead zirconate titanate (PZT) or the like is used. In the piezoelectric element 30A, the rear surface of the piezoelectric ceramics is formed with electrodes 31 (first electrode) and 31A (third electrode) with gaps 39 provided therebetween, and the front surface of the piezoelectric ceramics is formed with electrodes 32, 33, 34, 35, 36, and 37 (second electrodes) with gaps 55 provided between adjacent ones thereof. These electrodes 31, 31A, 32, 33, 34, 35, 36, and 37 are metal thin films, and can be formed by using a known technique, such as a technique of vapor-depositing or printing a metal, such as silver (Ag) or nickel (Ni), on the piezoelectric ceramics.

The electrode 31 of the illustrated piezoelectric element 30A has an open loop structure with the gaps 39 (gaps between opposite ends of the electrode 31 and opposite ends of the electrode 31A). Further, as described hereinafter with reference to FIG. 2C, the electrode 31A may be integrated into the electrode 31 to provide one gap 39 such that a C-shaped open loop structure is formed. In the present embodiment, the wording that the member A has an open loop structure means that the member A does not have an annular structure. Further, the annular structure in this case is not limited to a structure having an annular shape, but it may have any shape insofar as it is a structure in which a movement in one direction in the shape from a start point eventually passes the start point again.

The electrodes 32, 33, 34, 35, 36, and 37 are formed in a manner separate from each other with the gaps 55 as spaces therebetween. The electrodes 32 and 33 each have an arc length corresponding to a half-wavelength ($\lambda/2$), with the gap 55 included therein, and the electrodes 34, 35, 36, and 37 each have an arc length corresponding to a quarter-wavelength ($\lambda/4$), with the gap 55 included therein. Portions of the piezoelectric ceramics of the piezoelectric element 30A, which correspond to the electrodes 32, 34, and 36, respectively, are each polarized in a positive direction of the z direction (direction from the electrodes 32, 34, and 36 toward the electrode 31). Further, portions of the piezoelectric ceramics of the piezoelectric element 30A, which correspond to the electrodes 33, 35, and 37, respectively, are each polarized in a negative direction of the z direction (direction from the electrode 31 toward the electrodes 33, 35, and 37).

The piezoelectric element 30A is formed, at three locations, with through holes 38 which extend through the piezoelectric ceramics so as to electrically connect the electrodes formed on the front and rear surfaces of the piezoelectric ceramics. It is preferable that the through holes 38 are provided in an inner diameter side of the piezoelectric element 30A, at which strain is relatively small, and for example, the through holes 38 are formed inside a center circle D running as a centerline between respective circles having the inner and outer diameters of the piezoelectric element 30A. However, the through holes 38 can be formed outside the center circle D.

It is preferred that each through hole 38 is formed to be small as much as possible, and specifically, when the through hole 38 is formed by mechanical processing, if the piezoelectric ceramics has a thickness of approximately 0.5 mm, it is desirable that the through hole 38 has a diameter not larger than 1 mm (e.g. a diameter of 0.5 mm).

One of the three through holes 38 is provided for connecting the electrode 37 and the electrode 31A, and the other two are provided for connecting the electrodes 34 and 36, and the electrode 31. Electrical connection of the electrode 31 to the electrodes 34 and 36 is achieved using conductors 112 filled in the through holes 38 associated therewith, as described hereinafter with reference to FIGS. 5A to 5C, in which the electrode 31 is replaced by a common electrode 109 and one of the electrodes 34 and 36 is replaced by a non-driving electrode 110. Similarly, electrical connection of the electrode 37 to the electrode 31A is also achieved using the conductor 112 filled in the through hole 38 associated therewith. Note that by forming each through hole 38 as a cylindrical hole with high accuracy with respect to the outer shape of the piezoelectric ceramics, it is possible to use the through hole 38 as means for relatively positioning the electrodes, the gaps 55, and the gaps 39, which are provided on the front and rear surfaces of the piezoelectric ceramics.

For example, one of the electrodes 34 and 36 connected to the electrode 31, and the electrode 37 connected to the electrode 31A are set to the DC reference potential or the GND potential. Then, an A-phase AC voltage 17, shown in FIG. 4A, is applied to the electrodes 32, and a B-phase AC voltage 18 which is delayed in phase from the A-phase AC voltage 17 by $\pi/2$ rad is applied to the electrodes 33. As a consequence, travelling waves are generated on the elastic body 2, with an elliptic motion caused at a portion corresponding to a wave front of each travelling wave (a surface portion in contact with the driven element 3) of the elastic body 2, whereby it is possible to frictionally drive the driven element 3 for rotation. Further, by applying the A-phase AC voltage 17 to the electrodes 33, and applying the B-phase AC voltage 18 to the electrodes 32, it is possible to reverse the rotational direction of the driven element 3.

The electrode 35 is used as an electrode for detecting vibration. By acquiring a potential difference between the electrode 31 and the electrode 35, which is generated in proportion to the magnitude of strain of the vibration element, as a potential difference between one of the electrodes 34 and 36 connected to the electrode 31 and the electrode 35, it is possible to detect the vibration state of the vibration element.

Next, a description will be given of the piezoelectric element, denoted by reference numeral 30B, according to the second example of the configuration (hereafter referred to as "the second configuration example") shown in FIGS. 2C and 2D. The piezoelectric element 30B according to the second configuration example differs from the above-described piezoelectric element 30A according to the first configuration example in an electrode pattern and a polarization direction, and hence the description is given only of these points, and description redundant with that of the piezoelectric element 30A is omitted.

In the piezoelectric element 30B, the rear surface of the piezoelectric ceramics is provided with one gap 39, whereby the electrode 31 (first electrode) having a C-shaped open loop structure is formed. Further, the front surface of the piezoelectric ceramics is formed with electrodes 41, 42, 43, 44, 45, 46, 47, and 48 (second electrodes) with the gaps 55 therebetween. The electrodes 41 to 48 each have an arc length corresponding to a quarter-wavelength ($\lambda/4$), with the gap 55 included therein. Portions of the piezoelectric ceramics of the piezoelectric element 30B, which correspond to the electrodes 41 to 48, respectively, are polarized in the positive direction of the z direction, but may be polarized in the negative direction of the z direction.

The electrodes 45 and 48 are each formed with the through hole 38 inside the center circle D running as a centerline between respective circles having the inner and outer diameters of the piezoelectric element 30B. Electrical connection of the electrode 31 to the electrodes 45 and 48 is achieved using the conductors 112 filled in the through holes 38, as described hereinafter with reference to FIGS. 5A to 5C, in which the electrode 31 is replaced by the common electrode 109 and one of the electrodes 34 and 36 is replaced by the non-driving electrode 110. In the piezoelectric element 30B, the electrode 31 is used as the common electrode, an A(+)-phase AC voltage 19, shown in FIG. 4B, is applied to the electrodes 41, and a B(+)-phase AC voltage 20 which is delayed in phase from the A(+)-phase AC voltage 19 by $\pi/2$ rad is applied to the electrodes 42. Further, an A(−)-phase AC voltage 21 which is delayed in phase from the B(+)-phase AC voltage 20 by $\pi/2$ rad is applied to the electrodes 43, and a B(−)-phase AC voltage 22 which is delayed in phase from the A(−)-phase AC voltage 21 by $\pi/2$ rad is applied to the electrodes 44. As a consequence, travelling waves are generated on the elastic body 2, with an elliptic motion caused at a portion corresponding to a wave front of each wave (a surface portion in contact with the driven element 3) of the elastic body 2, whereby it is possible to frictionally drive the driven element 3 for rotation. Further, by interchanging the electrodes to which the A(+)-phase AC voltage 19 is applied and the electrodes to which the A(−)-phase AC voltage 21 is applied, it is possible to reverse the rotational direction of the driven element 3.

The electrodes 46 and 47 are used as electrodes for detecting vibration. By acquiring a potential difference between the electrode 31 and each of the electrodes 46 and 47, which is generated in proportion to the magnitude of strain of the vibration element, as a potential difference between one of the electrodes 45 and 48 connected to the electrode 31 and each of the electrodes 46 and 47, it is possible to detect the vibration state of the vibration element. The electrodes 46 and 47 are spatially shifted from each other by a quarter wavelength ($\lambda/4$), and hence by connecting the electrode 31 to the DC reference potential or the GND potential, it is possible to acquire the potential difference between each of the two electrodes 46 and 47 and the electrode 31, whereby it is possible to obtain more detailed vibration information of the vibration element.

In the piezoelectric element 30B, the piezoelectric ceramics is polarized in the same direction in all the portions corresponding to the electrodes 41 to 48. However, this is not limitative, but the polarization direction may be reversed between areas corresponding to the electrodes 41, 42, 45, and 46 and portions corresponding to the electrodes 43, 44, 47, and 48. In this case, the A-phase AC voltage 17 shown in FIG. 4A is applied to the electrodes 41 and 43, and the B-phase AC voltage 18 shown in FIG. 4A is applied to the electrodes 42 and 44, whereby it is possible to generate similar travelling waves. Further, in the piezoelectric element 30B, it is preferable to connect one of the electrodes 45 and 48 connected to the electrode 31 which is the common electrode to a GND terminal of voltage generation means, not shown. This makes it possible to stabilize the potential of the electrode 31, and increase the accuracy of signals from the electrodes 46 and 47 for vibration detection. Further, even in a case where the elastic body 2 is formed of a material which is slightly conductive, it is possible to suppress generation of a potential difference from the GND potential, at the elastic body 2 and part in contact with the elastic body 2.

Next, a description will be given of the piezoelectric element, denoted by reference numeral 30C, according to the third example of the configuration (hereafter referred to as "the third configuration example") shown in FIGS. 3A and 3B. The piezoelectric element 30C has a structure in which the rear surface of the piezoelectric ceramics having an arcuate shape is formed with the electrode 31 (first electrode) as the common electrode, and the front surface of the piezoelectric ceramics is formed with the electrodes 41, 42, 43, and 44 and electrodes 49, 50, and 51 (second electrodes) with the gaps 55 therebetween. The electrodes 41 to 44 and 50 each have an arc length corresponding to a quarter-wavelength ($\lambda/4$), with the gap 55 included therein. The electrodes 49 and 51 each have an arc length corresponding to a one-eighth wavelength ($\lambda/8$), with the gap 55 included therein.

Portions of the piezoelectric ceramics of the piezoelectric element 30C, which correspond to the electrodes 41 to 44 and 49 to 51, respectively, are polarized in the positive direction of the z direction, but may be polarized in the negative direction of the z direction. The electrodes 49 and 51 are each formed with the through hole 38 inside the center circle D running as a centerline between respective circles having the inner and outer diameters of the piezoelectric element 30C. The electrode 31 and the electrodes 49 and 51 are electrically connected to each other using the through holes 38, and are connected to the GND potential. The method of applying the AC voltages to the piezoelectric element 30C is the same as that used in the piezoelectric element 30B, and hence description thereof is omitted.

The electrode 50 is used as an electrode for detecting vibration. By acquiring a potential difference between the electrode 31 and the electrode 50, which is generated in proportion to the magnitude of strain of the vibration element, as a potential difference between one of the electrodes 49 and 51 connected to the electrode 31 and the electrode 50, it is possible to detect the vibration state of the vibration element. In the piezoelectric element 30C, portions of the electrodes 41 to 44 used for driving have a total area which is one sixth of a total area of the electrodes 41 to 44 used for driving in the piezoelectric element 30B. Therefore, it is preferred that the potential amplitude of the A(+)-phase AC voltage 19, the B(+)-phase AC voltage 20, the A(−)-phase AC voltage 21, and the B(−)-phase AC voltage 22 is set to a larger value, on an as-needed basis. Further, the vibration element may be formed by joining a plurality of piezoelectric elements 30C to the elastic body 2. Further, in the piezoelectric ceramics, the polarization direction may be reversed between portions corresponding to the electrodes 41 and 42, and portions corresponding to the electrodes 43 and 44. In this case, the A-phase AC voltage 17 is applied to the electrodes 41 and 43, and the B-phase AC voltage 18 is applied to the electrodes 42 and 44, whereby it is possible to generate similar travelling waves.

In the above description of the piezoelectric element 30A, the A-phase AC voltage 17 shown in FIG. 4A is applied to the electrodes 32, and the B-phase AC voltage 18 is applied to the electrodes 33, and the electrodes 31, 31A, 34, 36, and 37 are connected to the GND potential (or the DC reference potential). However, this is not limitative, but the AC voltage may be applied as the driving voltage to the electrodes 31, 31A, 34, 36, and 37.

Further, the piezoelectric element 30A can be driven by an A-phase AC voltage 23, a B-phase AC voltage 24 which is delayed in phase from the A-phase AC voltage by $\pi$ rad, and a C-phase AC voltage 25 which is advanced in phase from the A-phase AC voltage by $\pi/2$ rad, which are shown in FIG. 4C. In this case, the A-phase AC voltage 23 may be applied to the electrodes 32, the B-phase AC voltage 24 may be applied to the electrodes 33, and the C-phase AC voltage 25 may be applied to the electrodes 34, 36, and 37. In this case, the electrodes 31 and 31A which are electrically connected to the electrodes 34, 36, and 37 serve as the common electrode to the electrodes 32 and 33, and also serve as driving electrodes for applying the C-phase AC voltage 25. In this method, a potential difference between the electrodes 31 and 32 is indicated by an A-C-phase AC voltage 26 shown in FIG. 4D, and a potential difference given between the electrodes 31 and 33 is indicated by a B-C-phase AC voltage 27 shown in FIG. 4D. Thus, by setting the phase difference between the A-C-phase AC voltage 26 and the B-C-phase AC voltage 27 to $\pi/2$ rad, it is possible to generate travelling waves on the elastic body.

Figure 4D:
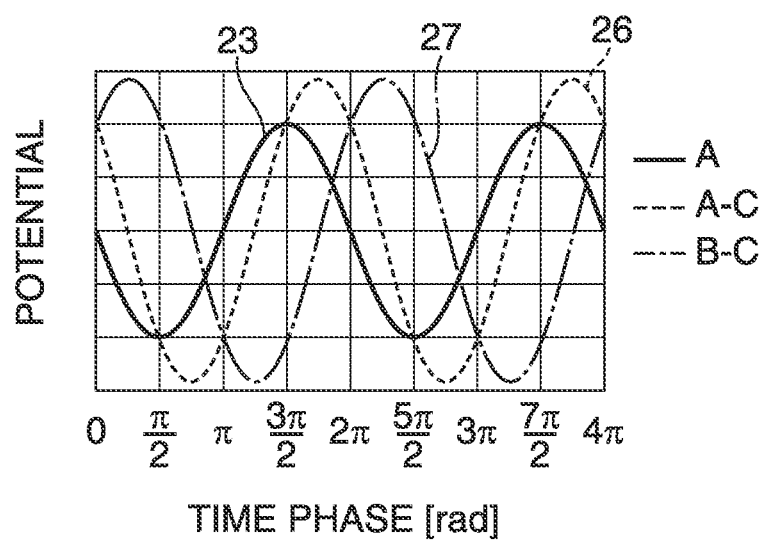
FIG. 4D is a diagram showing an example of a potential difference generated between the electrodes of the piezoelectric element.

When the A-phase AC voltage 23, the B-phase AC voltage 24, and the C-phase AC voltage 25 are equal in central potential and amplitude, as shown in FIG. 4D, the amplitude of the A-C-phase AC voltage 26 and the B-C-phase AC voltage 27 is theoretically equal to $2^{1/2}$ times the amplitude of the A-phase AC voltage 23. This makes it possible, even when the input voltage is limited, to increase the potential difference generated across the piezoelectric element 30A to thereby increase the vibration amplitude without increasing the input voltage. The method of setting sine waves which make the phase difference between the A-C-phase AC voltage 26 and the B-C-phase AC voltage 27 equal to 90 degrees is not limited to this, but it is possible to use a method of setting the A-phase AC voltage 23, the B-phase AC voltage 24, and the C-phase AC voltage 25 to desired waveforms each formed by superimposing a plurality of frequency components upon each other.

Further, although in the piezoelectric elements 30B and 30C, the electrode 31 is connected to the GND potential via the electrodes 45 and 48, this is not limitative, but the electrode 31 may be connected via the electrodes 45 and 48 to a DC reference potential which is not temporally varied. Further, the electrode 31 can be connected to an AC potential other than these, which has a desired waveform, and in this case, the electrode 31 functions as a common electrode to the electrodes 41 and 43, and to the electrodes 42 and 44.

The shape of each through hole 38 is not necessarily required to be circular in cross-section, but the through hole 38 is only required to form a conduction path communicating between the electrode 31 and an electrode opposed thereto (on the opposite surface of the piezoelectric element). For example, a conduction path can be formed by forming a groove cut into a U-shape, a V-shape, or a rectangular shape, in cross-section, in a side surface (an inner peripheral surface or an outer peripheral surface) of each of the piezoelectric elements 30A to 30C, and fixing a conductor in the groove.

Next, the electrode structure in the piezoelectric elements 30A to 30C will be described with reference to FIGS. 5A to 10B. Note that in the description given with reference to FIGS. 5A to 10B, the piezoelectric elements 30A to 30C are collectively referred to as the piezoelectric element 30. Accordingly, the electrodes provided on the rear surface of the piezoelectric ceramics in the piezoelectric elements 30A to 30C (electrodes shown in FIGS. 2A, 2C, and 3A) are referred to as the "common electrode" in the following description. Further, the electrodes provided on the front surface of the piezoelectric ceramics (electrodes shown in FIGS. 2B, 2D, and 3B) are referred to as the "non-driving electrodes" and the "driving electrodes" in the following description.

Figure 5A:
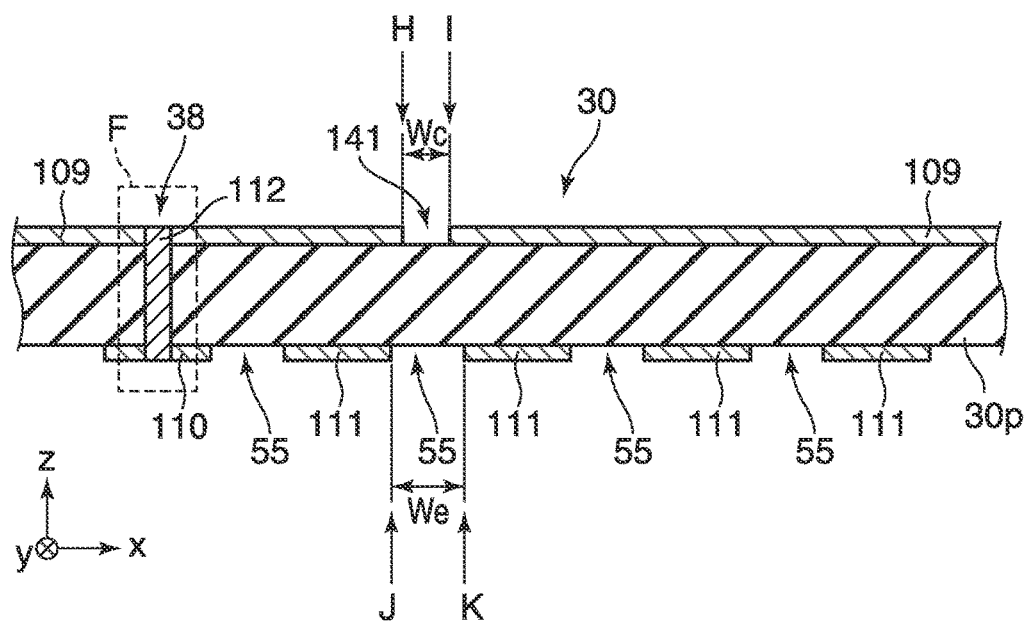
FIG. 5A is a partial cross-sectional view of a first electrode structure of the piezoelectric element.
Figure 5B:
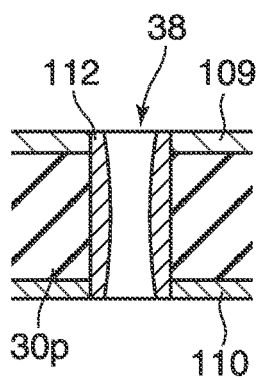
FIG. 5B is an enlarged view of an example of the construction of an area F in FIG. 5A.
Figure 5C:
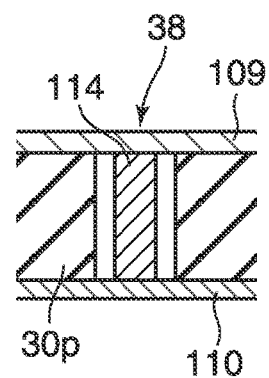
FIG. 5C is an enlarged view of another example of the construction of the area F in FIG. 5A.

FIG. 5A is a partial cross-sectional view of a first electrode structure of the piezoelectric element 30. In the first electrode structure of the piezoelectric element 30, the electrodes are formed on the front and rear surfaces of a piezoelectric body 30p formed of piezoelectric ceramics or the like. In the piezoelectric element 30, a surface (rear surface) via which the piezoelectric body 30p is joined to the elastic body 2, not shown in FIGS. 5A to 5C, is provided with the common electrode 109, and a surface (front surface) via which the piezoelectric body 30p is joined to the flexible circuit board 15, not shown in FIGS. 5A to 5C, is provided with the non-driving electrodes 110 and driving electrodes 111.

The common electrode 109 corresponds to the electrode 31 included in the piezoelectric elements 30A to 30C. The non-driving electrodes 110 correspond to the electrodes 34, 36, 37, 45, 48, 49, and 51, included in the piezoelectric elements 30A to 30C, and are used to connect the common electrode 109 to the GND potential. The driving electrodes 111 corresponds to the electrodes 32, 33, 35, 41, 42, 43, 44, 46, 47, and 50, included in the piezoelectric elements 30A to 30C, and are each used as the electrode for excitation or vibration detection. The above-mentioned relationship between the common electrode 109, the non-driving electrodes 110, and the driving electrodes 111, and the electrodes included in the piezoelectric elements 30A to 30C is similarly applied to the electrode structures described with reference to FIGS. 6 to 10B.

The common electrode 109 is a metallic film which is uniformly formed in the circumferential direction, but part of the common electrode 109 in the circumferential direction is cut away to form a gap 141. The gap 141 is an insulating portion corresponding to the gap 39 which divides the electrode 31 shown in FIG. 2C in the circumferential direction. The gap 141 may be formed by masking a predetermined area in advance when forming the common electrode 109, or may be formed by eliminating the part of the common electrode 109 by machining, such as grinding, after forming the common electrode 109 into a loop shape.

It is desirable that one end H of the gap 141 is at a location shifted in a positive direction of the x direction with respect to an end J of one driving electrode 111 and the other end I of the gap 141 is at a location shifted in a negative direction of the x direction with respect to an end K of the driving electrode 111, which is opposed to the end J in the x direction. That is, it is desirable that between a width Wc of the gap 141 and a width We of the gap 55, a relationship of "Wc≤We" holds, and the whole gap 141 is within the gap 55 when viewed in the z direction.

The gap 141 is a part which does not contribute to formation of an electric field in the piezoelectric element 30. Therefore, the gap 141 is provided at a location opposed to the gap 55 in the z direction, and the width Wc of the gap 141 is made narrower than the width We of the gap 55, whereby it is possible to reduce changes in electric field distribution due to the gap 141, and minimize degradation of excitation performance.

The through hole 38 is formed at one location so as to connect the common electrode 109 and the non-driving electrode 110. The inside of the through hole 38 is filled with the conductor 112, such as paste material containing silver (Ag), and the common electrode 109 and the non-driving electrodes 110 are electrically connected by the conductor 112. It is desirable that the conductor 112 is filled such that the conductor 112 does not rise higher than the common electrode 109 in the positive direction of the z direction so as prevent a crack or the like from being caused in the piezoelectric element 30 when the piezoelectric element 30 is joined to the elastic body 2.

The non-driving electrodes 110 are connected to the GND potential via the flexible circuit board 15, whereby the common electrode 109 is connected to the GND potential via the conductor 112 filled in the through hole 38. Therefore, even when the elastic body 2 has a high electrical resistance and does not function as a conductor, because the elastic body 2 is formed of e.g. one of an insulator, a semiconductor, and a composite material formed by causing an insulator or a semiconductor to contain a conductive material, it is possible to easily connect the common electrode 109 to the GND potential.

To prevent the conductor 112, which is exposed, from coming off or experiencing similar inconvenience, after the common electrode 109 and the non-driving electrodes 110 are electrically connected by the conductor 112, it is desirable that the piezoelectric element 30 is promptly joined to the elastic body 2 via the surface on which the common electrode 109 is provided or that the surface on which the common electrode 109 is provided is covered with a polyimide sheet or the like. Further, it is desirable that the piezoelectric element 30 is promptly joined to the flexible circuit board 15 via the surface on which the non-driving electrodes 110 are provided. This also applies to the electrode structures described hereinafter with reference to FIGS. 6 to 10B.

In the electrode structure shown in FIG. 5A, in a case where the piezoelectric element 30 is formed into a loop, the common electrode 109 can be formed into an open loop structure by providing the gap 141 therein. This makes it possible to prevent generation of a magnetic field due to a circular current flowing in the common electrode 109, and therefore, even when the vibration actuator is installed within a variable magnetic field environment, it is possible to prevent the variable magnetic field environment from being adversely affected. That is, it is possible to increase reliability of the vibration actuator when it is used in the variable magnetic field environment. This advantageous effect can be similarly obtained by the electrode structures having similar gaps, described hereinafter with reference to FIGS. 6 10B.

By using the gap 141 and the through hole 38 in combination, the gap 141 and the gap 55 can be relatively positioned with reference to the through hole 38, and for example, by forming the through hole 38 into a circular shape with high accuracy, it is possible to more precisely position the gap 141 and the gap 55. More specifically, as in the configuration shown in FIG. 2A, after forming the through hole 38, the common electrode 109 is formed with reference to the through hole 38, and similarly, the non-driving electrodes 110 and the driving electrodes 111 are formed such that the gaps 55 are arranged with reference to the through hole 38.

The position and width of the gap 141 are not limited to the form shown in FIGS. 5A to 5C. That is, even when a form in which the gap 141 and the gap 55 partially overlap or do not overlap at all when viewed in the z direction is employed, or even when the width Wc of the gap 141 and the width We of the gap 55 have a relationship of "Wc>We", there is no influence on the function of the through hole 38.

The configuration for using the through hole 38 as a conduction path for electrically connecting the common electrode 109 and each non-driving electrode 110 is not limited to the one in which the conductor 112 is filled in the whole inside of the through hole 38. FIGS. 5B and 5C correspond to an enlarged view of an area F in FIG. 5A, and each show another configuration in which the through hole 38 can be used as a conducive path.

FIG. 5B shows a configuration in which the conductor 112 is formed only on the inner wall of the through hole 38 to electrically connect the common electrode 109 and the non-driving electrode 110. In this case, the conductor 112 having a tubular shape may be hollow or may be filled with resin, such as an adhesive, which is an example of a dielectric (insulating) material.

FIG. 5C shows a configuration in which a solid conductor 114 made of a conductive bar or a conductive wire rod is inserted in the through hole 38, and the common electrode 109 and the non-driving electrode 110 are electrically connected to each other using the solid conductor 114. In this case, it is desirable that the solid conductor 114 is fixed by filling between the solid conductor 114 and the inner wall of the through hole 38 with a resin, such as an adhesive, silver paste, or the like material, irrespective of whether the material is conductive or not conductive. For example, the common electrode 109 is formed after forming the through hole 38 in the piezoelectric body 30p, and then the solid conductor 114 is inserted and fixed in the through hole 38 from the surface opposite to the surface on which the common electrode 109 is formed. After that, by forming the non-driving electrode 110, it is possible to realize the structure shown in FIG. 5C.

FIG. 6 is a partial cross-sectional view of a second electrode structure of the piezoelectric element 30. The electrode structure shown in FIG. 6 differs from the electrode structure shown in FIG. 5A in that the two through holes 38 are formed for the common electrode 109 and are each filled with the conductor 112, whereby the common electrode 109 is electrically connected to the two non-driving electrodes 110. The electrode structure shown in FIG. 6 is the same as the electrode structure in FIG. 5A, in the other respects, and hence the following description will be given only of the different point.

The two non-driving electrodes 110 are each formed with the through hole 38, and the inside of each through hole 38 is filled with the conductor 112. Thus, the common electrode 109 and the two non-driving electrodes 110 are electrically connected to each other via the conductors 112 filled in the through holes 38. As a consequence, even after the piezoelectric element 30 is joined to the elastic body 2 and the common electrode 109 is covered, it is possible, by directly applying tester probes to the two non-driving electrodes 110, to easily inspect conduction between the common electrode 109 and the two non-driving electrodes 110, and check electrical resistance therebetween. Further, even if a conduction failure occurs in one of the two conductors 112 after conduction inspection between the common electrode 109 and the non-driving electrodes 110, it is possible to maintain electrical connection of the common electrode 109 to the GND potential via the non-driving electrode 110 using the other conductor 112. This makes it possible to improve the reliability of the piezoelectric element 30 (vibration element). This advantageous effect can be similarly obtained in the electrode structures described hereinafter with reference to FIGS. 9A, 9B, 10A, and 10B. Further, when vibration is excited in the vibration element to drive the driven element 3, a large circular current does not flow through a closed loop, and therefore, even when the piezoelectric element 30 is disposed within a variable magnetic field environment, it is possible to reduce adverse influence, such as noise, on the variable magnetic field environment.

Note that the through hole 38 that is filled with the conductor 112 and electrically connects the common electrode 109 and the non-driving electrodes 110 is only required to be formed at two or more locations, and the number of through holes 38 is not limited to two. Further, although FIG. 6 shows a form in which the two driving electrodes 111 are provided between the non-driving electrodes 110 each formed with the through hole 38, the number of the driving electrodes 111 is not limited, and further, the non-driving electrodes 110 each formed with the through hole 38 may be arranged adjacent to each other with the gap 55 therebetween. It is obvious that the same advantageous effects can be obtained by the second electrode structure of the piezoelectric element 30, shown in FIG. 6, as provided by the first electrode structure described with reference to FIG. 5A.

FIG. 7 is a partial cross-sectional view of a third electrode structure of the piezoelectric element 30. The electrode structure shown in FIG. 7 differs from the electrode structure shown in FIG. 5A in that the configuration of the gap 141 provided in the common electrode 109 is changed such that an electrode 171 is provided between two gaps 172 and 173, but remains the same in the other respects. Therefore, the following description will be given only of the different point.

The common electrode 109 is formed along the whole circumference of the annular piezoelectric body 30p except the gaps 172 and 173, and the electrode 171. The gaps 172 and 173 can be formed by using the same method as that for forming the above-described gap 141, and the electrode 171 can be formed simultaneously with the common electrode 109. The electrode 171 is, in other words, an electrode portion remaining between the gaps 172 and 173 after the common electrode 109 is divided by the gaps 172 and 173.

It is desirable that an end H of the gap 172 toward the common electrode 109 is at a location shifted in a positive direction of the x direction with respect to an end J of one driving electrode 111 and an end I of the gap 173 toward the common electrode 109 is at a location shifted in a negative direction of the x direction with respect to an end K of the other driving electrode 111, which is opposed to the end J. That is, it is desirable that between the width Wc of an area including the gaps 172 and 173 and the electrode 171, and the width We of the gap 55, a relationship of "Wc≤We" holds, and an area including the gaps 172 and 173 and the electrode 171 is within the gap 55 when viewed in the z direction.

It is obvious that the electrode configuration shown in FIG. 7 provides the same advantageous effects as provided by the electrode configuration shown in FIG. 5A. Further, by providing the two gaps 172 and 173, it is possible to easily perform inspection for determining whether or not the common electrode 109 forms an open loop. More specifically, it is desirable that the width Wc of the area including the two gaps 172 and 173 and the electrode 171 is smaller than the width We of the gap 55, and hence as the width We becomes smaller, the widths of the gaps 172 and 173 are reduced. Here, there is a fear that opposed ends of the common electrode 109 may connect via the electrode 171 to form a closed loop, depending on the accuracy of formation of the two gaps 172 and 173. However, by directly applying tester probes to the common electrode 109 and the electrode 171, it is possible to easily inspect whether or not the common electrode 109 forms an open loop (whether or not the conduction loop is positively electrically disconnected).

The potential of the electrode 171 formed between the gaps 172 and 173 is unstable, and hence from a viewpoint of safety, such as avoidance of abrupt discharging, it is desirable to cover the whole surface of the electrode 171 with the elastic body 2, or connect the electrode 171 to the GND potential by a method in which the through hole 38 is not used. As an example of the method in which the through hole 38 is not used, a thin sheet metal is disposed between the electrode 171 and the elastic body 2, and this thin sheet metal is connected to the GND potential. Further, there may be used a method of providing a conduction path which can be electrically connected to the electrode 171, on the elastic body 2 in a localized manner.

After it is confirmed that the common electrode 109 forms an open loop, the two gaps may be changed to one gap by leaving one of the gaps 172 and 173 which positively insulate between the common electrode 109 and the electrode 171, as it is, and coating the other with e.g. paste-like conductive material. This makes it possible to eliminate a situation in which the electrode 171 becomes unstable in potential. This method can be applied to the configuration described hereinafter with reference to FIGS. 9A and 9B.

Figure 8:
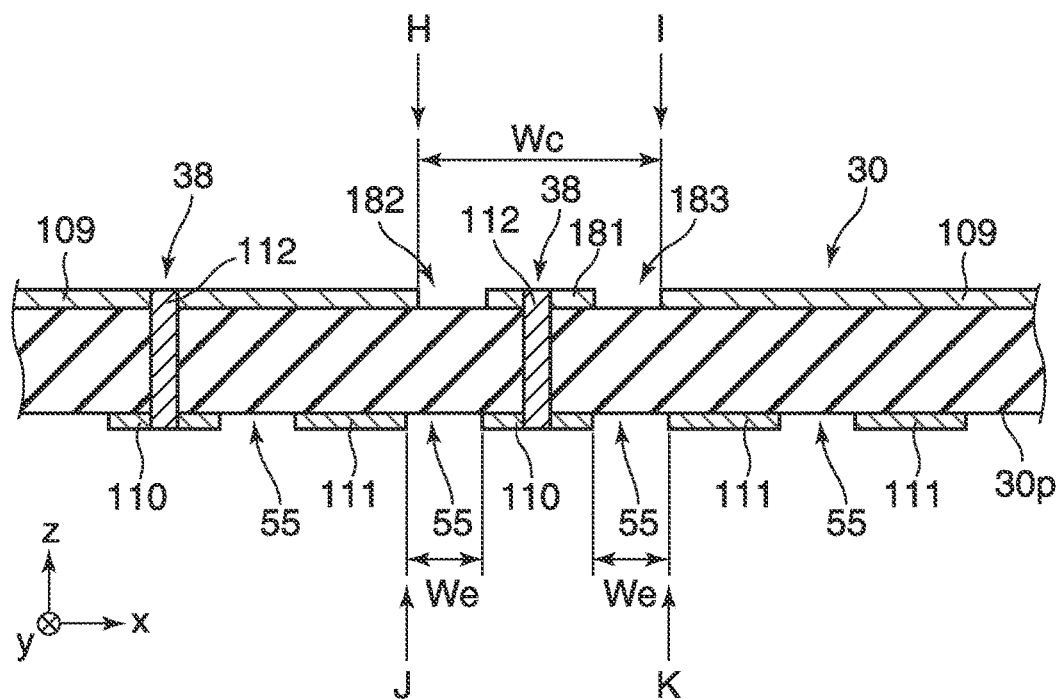
FIG. 8 is a partial cross-sectional view of a fourth electrode structure of the piezoelectric element.

FIG. 8 is a partial cross-sectional view of a fourth electrode structure of the piezoelectric element 30. The electrode structure shown in FIG. 8 differs from the electrode structure shown in FIG. 5A in that, firstly, the configuration of the gap 141 formed in the common electrode 109 shown in FIGS. 5A to 5C is changed such that an electrode 181 is provided between two gaps 182 and 183, which are insulating portions, and secondly, the electrode 181 provided between the two gaps 182 and 183 is electrically connected to the non-driving electrode 110 by the conductor 112 filled in the through hole 38. The electrode structure shown in FIG. 8 is the same in the other respects as the electrode structure in FIG. 5A, and hence the following description will be given only of the different point.

The common electrode 109 is formed along the whole circumference of the annular piezoelectric body 30p except the gaps 182 and 183, and the electrode 181. The gaps 182 and 183 can be formed by the same method as that for forming the gap 141 described with reference to FIGS. 5A to 5C, and the electrode 181 can be formed simultaneously with the common electrode 109. It is desirable that an end H of the one gap 182 is at a location shifted in a positive direction of the x direction with respect to an end J of one driving electrode 111 opposed thereto in the z direction, and an end I of the other gap 183 toward the common electrode 109 is at a location shifted in a negative direction of the x direction with respect to an end K of another driving electrode 111 opposed thereto in the z direction, which end is opposed to the end J. Further, it is desirable that the gaps 182 and 183 and the electrode 181 are provided in an area opposed to an area in the z direction, in which are formed the non-driving electrode 110 and the gaps 55 which do not contribute to electric field formation for excitation.

The configuration in which the electrode 181 is provided between the two gaps 182 and 183 has the same function as the configuration, described with reference to FIG. 7, in which the electrode 171 is provided between the two gaps 172 and 173. Therefore, the fourth electrode structure shown in FIG. 8 as well provides the same advantageous effects as provided by the third electrode structure shown in FIG. 7. Further, the electrode 181 appearing in FIG. 8 is electrically connected to the non-driving electrode 110 and is maintained at the GND potential, and hence it is possible to eliminate an electrode which is unstable in potential. In the electrode which is unstable in potential, apparent rigidity is changed by an inverse piezoelectric effect due to changes in potential caused by changes in internal stress of the piezoelectric element 30. Partial change in rigidity differentiates the resonance frequency between the two vibration modes for forming travelling waves generated on the vibration element, which lowers the performance of the vibration actuator, and hence by maintaining the electrode 181 at the GND potential, it is possible to avoid this problem. This effect can be more markedly obtained with respect to the electrode 181 which is larger in width than the electrode 171.

Figure 9A:
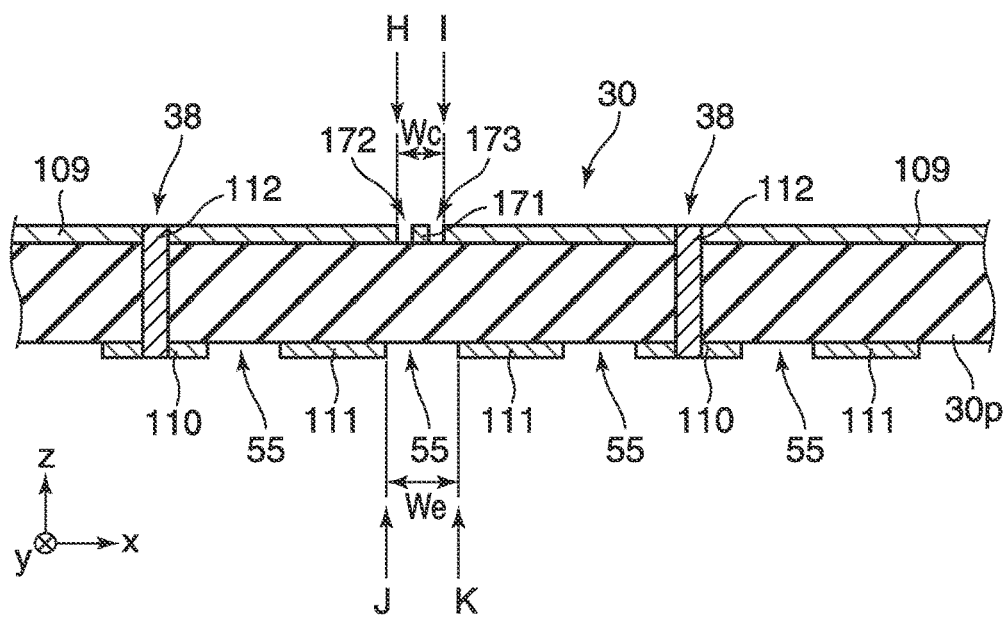
FIG. 9A is a partial cross-sectional view of a fifth electrode structure of the piezoelectric element.

FIG. 9A is a partial cross-sectional view of a fifth electrode structure of the piezoelectric element 30. The electrode structure shown in FIG. 9A has a structure formed by combining the electrode structure shown in FIG. 6 and the electrode structure shown in FIG. 7. That is, the electrode structure shown in FIG. 9A differs from the electrode structure shown in FIG. 5A in that the configuration of the gap 141 formed in the common electrode 109 is changed such that the electrode 171 is provided between the two gaps 172 and 173. Further, the electrode structure shown in FIG. 9A differs from the electrode structure shown in FIG. 5A in that the two through holes 38 each filled with the conductor 112 are provided for the common electrode 109, and the common electrode 109 and the two non-driving electrodes 110 are electrically connected to each other via the conductors 112.

These different points have already been described, and hence description thereof is omitted. Further, it is obvious that the electrode structure shown in FIG. 9A provides both of the advantageous effects provided by the electrode structure shown in FIG. 6 and those provided by the electrode structure shown in FIG. 7.

Figure 9B:
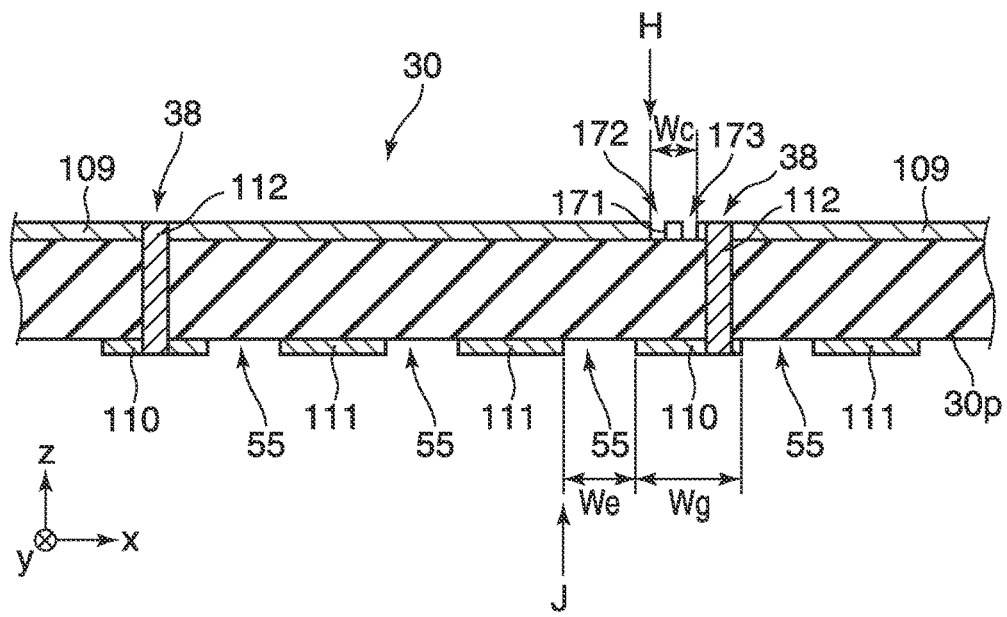
FIG. 9B is a partial cross-sectional view of a variation of the fifth electrode structure of the piezoelectric element.

The electrode structure shown in FIG. 9A can be transformed into an electrode structure shown in FIG. 9B. More specifically, the area including the gaps 172 and 173 and the electrode 171 may be provided at a location opposed to the non-driving electrode 110 in the z direction, and also the non-driving electrode 110 may be electrically connected to the common electrode 109 via the conductor 112 filled in the through hole 38.

In this case, it is only required that the gaps 172 and 173 and the electrode 171 are formed in a range opposed in the z direction to an area indicated by the sum of a width Wg of the non-driving electrode 110 and the width We of the gap 55 (=We+Wg). In other words, the area including the gaps 172 and 173 and the electrode 171 is arranged so as to avoid a location opposed to the driving electrode 111 used for excitation or vibration detection. This makes it possible to increase the allowance of dimensional accuracy required when forming the gaps 172 and 173, and further, it is possible to minimize degradation of excitation performance caused due to the area including the 172 and 173 and the electrode 171, which does not contribute to electric field formation for driving.

Figure 10A:
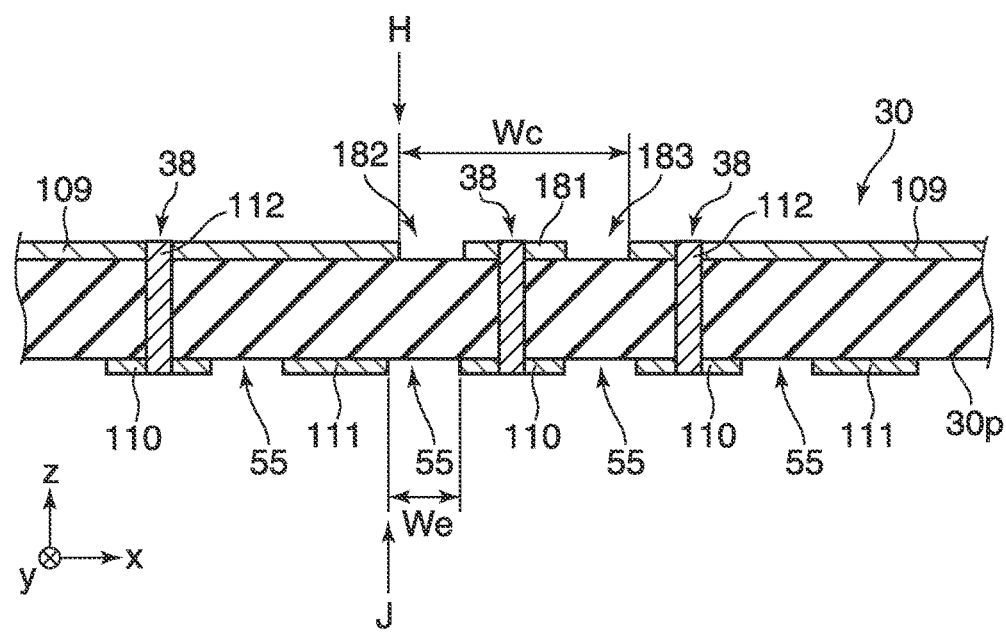
FIG. 10A is a partial cross-sectional view of a sixth electrode structure of the piezoelectric element.

FIG. 10A is a partial cross-sectional view of a sixth electrode structure of the piezoelectric element 30. The electrode structure shown in FIG. 10A has a structure formed by combining the electrode structure shown in FIG. 6 and the electrode structure shown in FIG. 8, and differs from that shown in FIG. 5A in the following three points: Firstly, the three through holes 38 each filled with the conductor 112 are provided in the common electrode 109, and the common electrode 109 is electrically connected to the three non-driving electrodes 110 by the conductors 112 in the through holes 38. Secondly, the configuration of the gap 141 formed in the common electrode 109 is changed such that the electrode 181 is provided between the two gaps 182 and 183. Thirdly, the electrode 181 is electrically connected to the non-driving electrode 110 via the conductor 112 filled in the through hole 38.

These different points have already been described, and hence description thereof is omitted. Further, it is obvious that the electrode structure shown in FIG. 10A provides both of the advantageous effects provided by the electrode structure shown in FIG. 6 and those provided by the electrode structure shown in FIG. 8. Further, by providing the conduction paths formed by the three through holes 38 each filled with the conductor 112, it is possible to perform both of conduction inspection of the conduction paths and inspection of disconnection of the loop of the common electrode 109.

Figure 10B:
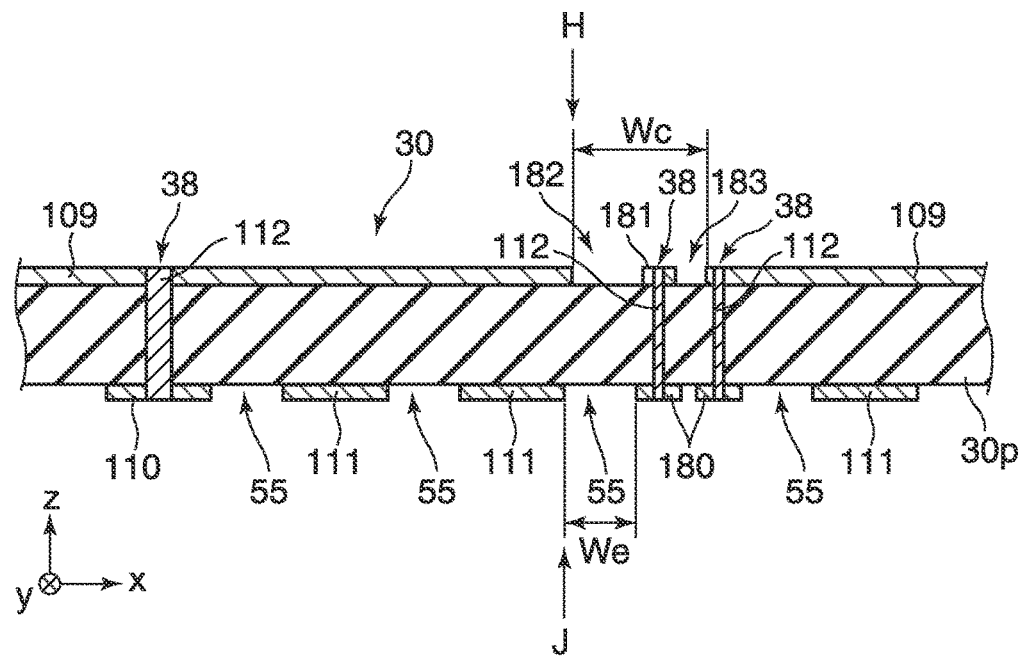
FIG. 10B is a partial cross-sectional view of a variation of the sixth electrode structure of the piezoelectric element.

The electrode structure shown in FIG. 10A can be transformed into an electrode structure shown in FIG. 10B. More specifically, one non-driving electrode 110 is changed into two non-driving electrodes 180 which each have a narrower width and are electrically independent of each other. Further, one of the two non-driving electrodes 180 is electrically connected to the common electrode 109 by the conductor 112 filled in the through hole 38 associated therewith, and the other is electrically connected to the electrode 181 by the conductor 112 filled in the through hole 38 associated therewith. In doing this, the width of the gap 182 and the width of the gap 183 are changed such that an end H of the gap 182 is at a location shifted in a positive direction of the x direction with respect to the end J of the driving electrode 111 in FIG. 10B.

In the electrode structure shown in FIG. 10B, it is possible not only to obtain the same advantageous effects as provided by the electrode structure shown in FIG. 10A, but also to reduce the area which does not contribute to electric field formation, compared with the electrode structure shown in FIG. 10A. Therefore, it is possible to increase the area of regions assigned to the electrodes for excitation or vibration detection, and thereby increase the driving performance and the control performance.

Next, a description will be given of a medical system provided with the above-described vibration actuator 1. In this medical system, a medical manipulator provided with the vibration actuator 1 is applied to an MRI diagnostic apparatus that performs diagnosis, measurement, and medical treatment, using a magnetic field space.

Figure 11A:
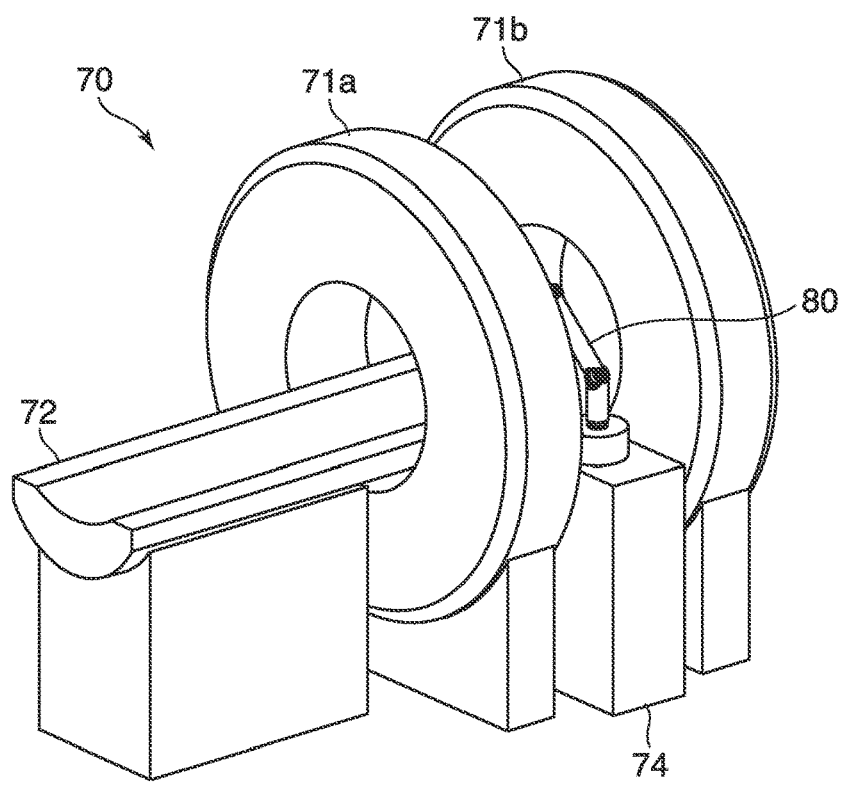
FIG. 11A is a schematic perspective view of an MRI diagnostic apparatus provided with a manipulator including the vibration actuator.
Figure 11B:
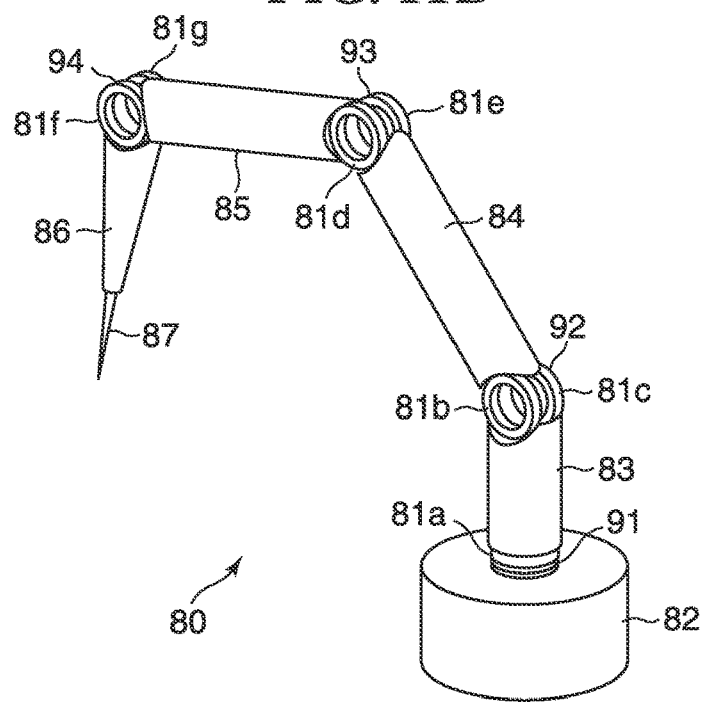
FIG. 11B is a schematic perspective view of the manipulator.

FIG. 11A is a schematic perspective view of an MRI diagnostic apparatus 70 provided with a manipulator 80. FIG. 11B is a schematic perspective view of the manipulator 80. As the MRI diagnostic apparatus 70, FIG. 11 shows an open-type MRI diagnostic apparatus in which two superconductive magnets are combined into a double-doughnut shape to from a magnetic field generation unit. The MRI diagnostic apparatus 70 includes hollow cylindrical magnets 71a and 71b, a treating table 72 on which a patient lies, and a manipulator stand 74 on which the manipulator 80 is set. In the MRI diagnostic apparatus 70, the manipulator 80, which is an articulated robot, is set between the hollow cylindrical magnets 71a and 71b, and it is possible to perform medical treatment using the manipulator 80 while acquiring image information of a subject.

The manipulator 80 has a four-axis vertical articulated arm structure in which a first arm 83, a second arm 84, a third arm 85, and a fourth arm 86 are connected via a first joint 91, a second joint 92, a third joint 93, and a fourth joint 94, each of which has one degree of freedom of rotation. The first joint 91 is mounted on a base 82.

A vibration actuator 81a is assembled to the first joint 91, vibration actuators 81b and 81c are assembled to the second joint 92, vibration actuators 81d and 81e are assembled to the third joint 93, and vibration actuators 81f and 81g are assembled to the fourth joint 94. The vibration actuator 1 described with reference to FIGS. 1A to 1C is used as each of these vibration actuators 81a to 81g, and the piezoelectric element 30 described with reference to FIGS. 5A to 10B is used in each of the vibration actuators 81a to 81g. The vibration actuators 81a to 81g drive the joints associated therewith, whereby each joint is enabled to perform rotational movement.

An end effector 87 that performs desired medical treatment operations, such as puncture, cauterization, and holding, is attached to an extremity of the fourth arm 86. Examples of the end effector 87 include a medical knife, a forceps, a needle, a probe, and diagnosis instruments, but are not particularly limited, and the medical treatment includes not only treatment, such as an operation, but also diagnosis.

The vibration actuators 81a to 81g each include the supporting member 7 and the flange 8, described with reference to FIGS. 1A to 1C. The supporting member 7 of the vibration actuator 81a is fixed to the base 82, and the flange 8 of the vibration actuator 81a is fixed to the first arm 83, whereby the vibration actuator 81a applies a rotational torque to the first arm 83, for rotation thereof about the rotational axis of the first joint 913. The supporting members 7 of the vibration actuators 81b and 81c are both fixed to the first arm 83, and the flanges 8 of the same are both fixed to the second arm 84, whereby the vibration actuators 81b and 81c apply a rotational torque to the second arm 84, for rotation thereof about the rotational axis of the second joint 92. The supporting members 7 of the vibration actuators 81d and 81e are both fixed to the second arm 84, and the flanges 8 of the same are both fixed to the third arm 85, whereby the vibration actuators 81d and 81c apply a rotational torque to the third arm 85, for rotation thereof about the rotational axis of the third joint 93. The supporting members 7 of the vibration actuators 81f and 81g are both fixed to the third arm 85, and the flanges 8 of the same are both fixed to the fourth arm 86, whereby the vibration actuators 81f and 81g apply a rotational torque to the fourth arm 86, for rotation thereof about the rotational axis of the fourth joint 94.

As described above, by arranging the vibration actuator in each joint, it is possible to omit a power transmission mechanism, such as gears and belts, whereby it is possible to increase the responsiveness of the manipulator 80. Further, by arranging a plurality of vibration actuators in the joint, it is possible to obtain a large rotational torque and a large holding torque. Note that in a case where a sufficient rotational torque and a sufficient holding torque can be obtained by one vibration actuator, it is not necessary to construct the joint using a plurality of vibration actuators.

It is desirable that the vibration actuators 81a to 81g as the components of the manipulator 80 use non-magnetic materials for all component members, except the material of wiring of the flexible circuit board 15 for applying voltages to the piezoelectric element 30 and the material of the electrodes of the piezoelectric element 30. For this reason, the base 82, the first arm 83, the second arm 84, the third arm 85, and the fourth arm 86 are formed of non-magnetic materials.

Further, it is preferred that the component members of the vibration actuators 81a to 81g are configured such that none of them have a closed loop. For example, if a metallic material is used for the annular driven element 3, a closed loop is inevitably formed, but it is possible to realize the configuration having no closed loop by using a dielectric, such as resin or ceramics, for the driven element 3. Further, as described with reference to FIGS. 5A to 10B, the electrode structure of the piezoelectric element 30 used in each of the vibration actuators 81a to 81g is an open loop structure. Therefore, even when the manipulator 80 is installed in the vicinity of the hollow cylindrical magnets 71*a* and 71*b* of the MRI diagnostic apparatus 70, it is possible to minimize the influence of the manipulator 80 on the magnet field of the MRI diagnostic apparatus 70. This makes it possible to reduce artifacts and noise of an image acquired by the MRI diagnostic apparatus 70.

When the manipulator 80 is arranged within the MRI diagnostic apparatus 70, a variable magnetic field generated by the MRI diagnostic apparatus 70 may penetrate respective planes of the vibration actuators 81*a* to 81*g* (X-Y plane shown in FIGS. 1A to 1C). However, since a conductive closed loop is not formed in the annular piezoelectric elements 30 of the vibration actuators 81*a* to 81*g*, it is possible to reduce a risk that a magnetic field generated due to generation of an induced electromotive force disturbs a magnetic field of the MRI diagnostic apparatus, which is controlled with high accuracy. Further, when a variable magnetic field penetrates a closed loop, electromagnetic waves caused by temporal changes in all magnetic fluxes penetrating the closed loop are generated, but by avoiding formation of a closed loop in the electrode structure, it is possible to suppress generation of such electromagnetic waves, and reduce noise having an influence on the MRI diagnostic apparatus 70 and the peripheral devices. Further, when a variable magnetic field penetrates a closed loop, the Lorentz force generated due to temporal changes in all magnetic fluxes penetrating the closed loop causes a mechanical vibration in the vicinity thereof, but by avoiding formation of a closed loop in the electrode structure, it is possible to reduce generation of such a mechanical vibration in the manipulator 80.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

For example, in the above-described embodiment, in a case where the common electrode 109 on the rear surface of the piezoelectric element 30 is electrically connected to the electrode on the front surface via the through hole 38, the common electrode 109 is connected to the GND potential. However, this is not limitative, but the common electrode 109 may be connected to the DC reference potential, or may be connected to the C-phase AC voltage 25 shown in FIG. 4 or any other driving voltage having a desired waveform. Further, in the piezoelectric element 30, by connecting the non-driving electrodes 110 and 180 to the GND potential, and measuring the capacitance and admittance of the driving electrode 111 using e.g. an impedance analyzer, it is possible to indirectly inspect conduction between the common electrode 109 and the non-driving electrode 110.

Further, although in the above-described embodiment, as the MRI diagnostic apparatus 70, the example has been described in which the manipulator 80 is installed within the apparatus which is of the open-type and also has the double-doughnut shape, this is not limitative, but the MRI diagnostic apparatus may have any other structure. For example, the MRI diagnostic apparatus to which the manipulator 80 can be applied may be of an open type having a hamburger-like shape, or a tunnel type. Further, although in the above-described embodiment, as the manipulator 80, the one having the four-axis vertical articulated structure is described by way of example, this is not limitative, but the manipulator may be of a horizontal articulated type or a parallel link mechanism type, and none of the degree of freedom of rotation, a place where the vibration actuator is installed, and the number of vibration actuators are limited.

Further, although in the manipulator 80, the vibration actuator 1 of the rotary drive type is directly disposed in each joint, as the vibration actuator, a device of a direct drive type, an in-plane drive type, or a spherical drive type may be used. Further, a drive torque may be applied to a joint using a power transmission mechanism. Furthermore, all or part of the drive sources of the manipulator 80 may be provided within the base 82, and a torque may be applied to each joint via the power transmission mechanism. This makes it possible to reduce the weight of the movable sections of the manipulator 80, and increase the responsiveness.

This application claims the benefit of Japanese Patent Application No. 2015-114697 filed Jun. 5, 2015, which is hereby incorporated by reference herein in its entirety.

What is claimed is:

1. A vibration actuator in which a vibration element and a driven element are in contact with each other, with relative movement being effected between the driven element and the vibration element, the vibration element comprising:
an elastic body of which a main ingredient comprises a material which is electrically insulating, dielectric, or semi-conductive, said elastic body being in contact with the driven element; and
an electromechanical energy conversion element that is joined to said elastic body, said electromechanical energy conversion element comprising:
a piezoelectric body;
a first electrode that is provided on a surface of said piezoelectric body, through which surface said piezoelectric body is joined to said elastic body, said first electrode having a first gap to form an open loop structure;
at least two second electrodes that are provided in a manner opposed to said first electrode via said piezoelectric body;
at least one third electrode that is provided in a manner opposed to said first electrode via said piezoelectric body; and
at least one conduction path that electrically connects said first electrode and said at least one third electrode,
wherein a second gap is formed between said at least two second electrodes, and
wherein when viewed in a direction along which the vibration element is pressed against the driven element, a width of the first gap is narrower than a width of the second gap.

2. The vibration actuator according to claim 1, further comprising a fourth electrode that is formed on the surface of said piezoelectric body, through which surface said piezoelectric body is joined to said elastic body, such that said fourth electrode is formed in the first gap.

3. The vibration actuator according to claim 2, wherein said at least one third electrode is provided in a manner opposed to said fourth electrode via said piezoelectric body, and
wherein a conduction path electrically connects said fourth electrode and said at least one third electrode.

4. The vibration actuator according to claim 3, wherein said at least one third electrode, which is electrically connected to said fourth electrode, is connected to a GND potential.

5. The vibration actuator according to claim 2, wherein said fourth electrode is provided (i) at a location opposed to the second gap or (ii) at a location opposed to said at least one third electrode, which is electrically connected to said first electrode.

6. The vibration actuator according to claim 1, wherein said first electrode is electrically connected to two third electrodes of said at least one third electrode via at least two said conduction paths.

7. The vibration actuator according to claim 1, wherein said at least one third electrode is connected to a GND potential.

8. The vibration actuator according to claim 1, wherein an electrode for vibration detection, which indicates a potential dependent on a magnitude of strain of said elastic body, is provided on a surface of said piezoelectric body on which surface said at least two second electrodes are provided.

9. The vibration actuator according to claim 1, wherein a surface of said piezoelectric body, on which surface said at least two second electrodes are provided, is covered with a flexible circuit board having wiring for applying a voltage.

10. The vibration actuator according to claim 1, wherein said at least one conduction path is formed by providing a conductor inside a through-hole formed through said piezoelectric body or by fixing a conductor in a groove formed in a side surface of said piezoelectric body.

11. The vibration actuator according to claim 10, wherein said piezoelectric body has an annular shape, and
wherein said at least one conduction path is provided inside a center circle running as a centerline between respective circles having inner and outer diameters of said piezoelectric body.

12. The vibration actuator according to claim 1, wherein the main ingredient of said elastic body comprises the electrically insulating material.

13. The vibration actuator according to claim 1, wherein the driven element is formed of a material which is electrically insulating, dielectric, or semi-conductive.

14. A medical system including:
an articulated robot that performs diagnosis or an operation on a subject, said articulated robot having a plurality of joints; and
a vibration actuator in which a vibration element and a driven element are in contact with each other, with relative movement being effected between said driven element and said vibration element, said vibration actuator being assembled into at least one of said joints for enabling said joint to perform rotational movement,
said vibration element comprising:
an elastic body of which a main ingredient comprises a material which is electrically insulating, dielectric, or semi-conductive, said elastic body being in contact with the driven element; and
an electromechanical energy conversion element that is joined to said elastic body, said electromechanical energy conversion element comprising:
a piezoelectric body;
a first electrode that is provided on a surface of said piezoelectric body, through which surface said piezoelectric body is joined to said elastic body, said first electrode having a first gap to form an open loop structure;
at least two second electrodes that are provided in a manner opposed to said first electrode via said piezoelectric body;
at least one third electrode that is provided in a manner opposed to said first electrode via said piezoelectric body; and
at least one conduction path that electrically connects said first electrode and said at least one third electrode,
wherein a second gap is formed between said at least two second electrodes, and
wherein when viewed in a direction along which the vibration element is pressed against the driven element, a width of the first gap is narrower than a width of the second gap.

15. The medical system according to claim 14, further comprising a magnetic field generation unit configured to generate a magnetic field, and
wherein said articulated robot is arranged within or in the vicinity of the magnetic field generated by said magnetic field generation unit.

16. The medical system according to claim 14, further comprising a fourth electrode that is formed on the surface of said piezoelectric body, through which surface said piezoelectric body is joined to said elastic body, such that said fourth electrode is formed in the first gap.

17. The medical system according to claim 16, wherein said at least one third electrode is provided in a manner opposed to said fourth electrode via said piezoelectric body, and
wherein a conduction path electrically connects said fourth electrode and said at least one third electrode.

18. The medical system according to claim 17, wherein said at least one third electrode, which is electrically connected to said fourth electrode, is connected to a GND potential.

19. The medical system according to claim 16, wherein said fourth electrode is provided (i) at a location opposed to the second gap or (ii) at a location opposed to said at least one third electrode, which is electrically connected to said first electrode.

20. The medical system according to claim 14, wherein said first electrode is electrically connected to two third electrodes of said at least one third electrode via at least two said conduction paths.

21. The medical system according to claim 14, wherein said at least one third electrode is connected to a GND potential.

22. The medical system according to claim 14, wherein the main ingredient of said elastic body comprises the electrically insulating material.

* * * * *